(12) United States Patent
Lin et al.

(10) Patent No.: US 10,487,119 B2
(45) Date of Patent: Nov. 26, 2019

(54) PEPTIDES FOR DIAGNOSIS AND TREATMENT OF CANCER

(71) Applicant: National Taiwan University, Taipei (TW)

(72) Inventors: Chin-Tarng Lin, Taipei (TW); Han-Chung Wu, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 196 days.

(21) Appl. No.: 15/497,851

(22) Filed: Apr. 26, 2017

(65) Prior Publication Data

US 2017/0283468 A1    Oct. 5, 2017

Related U.S. Application Data

(63) Continuation-in-part of application No. 14/165,358, filed on Jan. 27, 2014, now abandoned.

(30) Foreign Application Priority Data

Oct. 18, 2013    (TW) .............................. 102137765 A

(51) Int. Cl.

| A61K 38/16 | (2006.01) |
| A61K 38/00 | (2006.01) |
| A61K 47/64 | (2017.01) |
| A61K 51/08 | (2006.01) |
| C07K 7/06 | (2006.01) |
| C07K 7/08 | (2006.01) |
| C07K 14/00 | (2006.01) |
| C07K 14/005 | (2006.01) |
| A61K 39/395 | (2006.01) |
| C07H 21/04 | (2006.01) |
| C12N 5/07 | (2010.01) |
| C12N 9/00 | (2006.01) |

(52) U.S. Cl.
CPC ............ *C07K 14/005* (2013.01); *A61K 38/16* (2013.01); *A61K 39/395* (2013.01); *A61K 51/088* (2013.01); *C07H 21/04* (2013.01); *C07K 7/06* (2013.01); *C12N 5/06* (2013.01); *A61K 38/00* (2013.01); *C12N 9/00* (2013.01)

(58) Field of Classification Search
CPC ...... A61K 38/00; A61K 38/16; A61K 39/395; A61K 47/64; A61K 51/088; A61K 51/08; C07K 14/005; C07K 7/06; C07K 7/08
USPC .......................................................... 514/1.1
See application file for complete search history.

(56) References Cited

U.S. PATENT DOCUMENTS

| 7,238,665 | B2 * | 7/2007 | Wu ...................... | A61K 9/1271 424/450 |
| 8,088,887 | B2 * | 1/2012 | Wu ...................... | A61K 9/1271 530/300 |

* cited by examiner

*Primary Examiner* — Julie Ha
(74) *Attorney, Agent, or Firm* — WPAT, PC

(57) ABSTRACT

A method of peptide histochemical diagnosis to detect the peptide binding protein in the cancer tissue is described. This peptide binding specifically to tumor cells is linked to the dextran coated iron oxide nanoparticle. The peptide linked dextran coated iron oxide nanoparticle can be used to bind to the formalin-fixed and paraffin-embedded tumor surgical specimens, and the method of present disclosure can be used to evaluate the efficacy of peptide-targeted chemotherapy for treatment of cancer patients.

6 Claims, 17 Drawing Sheets
(17 of 17 Drawing Sheet(s) Filed in Color)
Specification includes a Sequence Listing.

A  B

C  D

PEPTIDES FOR DIAGNOSIS AND TREATMENT OF CANCER

CROSS-REFERENCE TO RELATED APPLICATIONS

This application is a continuation-in-part of U.S. patent application Ser. No. 14/165,358, filed on Jan. 27, 2014, which claims the priority benefit of Taiwan application serial No. 102137765, filed on 18 Oct. 2013 and now granted as patent No. TW 1491881. The disclosure of the Taiwan application is incorporated by reference herein.

BACKGROUND OF THE INVENTION

1. Field of the Invention

The invention relates to a method for peptide histochemical diagnosis, and in particular, to a method for peptide histochemical diagnosis of the formalin-fixed paraffin-embedded surgical specimens.

2. The Prior Arts

Currently, some targeted peptides for the targeted chemotherapy in cancers have been reported. However, it is difficult to identify whether the peptides can be used to bind to the peptide binding protein in cancer cells by staining the formalin-fixed paraffin-embedded surgical specimens, to confirm the peptides for the targeted chemotherapy in cancers has efficacy in patients before clinical use. Although the patients suffer the same type of cancer, it is still unknown that the peptides for the targeted chemotherapy in different patient cancers can really bind to the individual cancer cells of the patients due to the individual difference. Therefore, to identify whether the peptide can bind to the cancer cells of each patient before chemotherapy, it will be extremely beneficial for the efficacy of peptide-targeted chemotherapy.

Thus, it is the key to evaluate therapy effects of the patient before peptide-targeted chemotherapy, and the main problem is to identify whether the targeted peptide can directly bind to the surgical tumor specimens from the patient. Moreover, the peptides have the following characteristics: a. The peptides can bind to different and undifferentiated nasopharyngeal carcinoma (NPC) or other cancer cells; b. The peptides targeted chemotherapy can make tumor shrink; c. The peptides can not bind to the normal cells in the normal organ tissue. It has been reported that biotin can be directly linked to the peptide to form a biotin-peptide, the biotin-peptide can also bind to cancer cells, but it has poor result in the paraffin-embedded surgical specimens. The biotin-peptide can bind to the small surgical specimens a little, and the binding capability is very weak than that of general antibodies, especially, biotin-peptide almost can not bind to more than 1 cm in diameter of the surgical specimens. The main reason is that the surgical specimens are formalin-fixed paraffin-embedded surgical sections, and there are only three amino acids of the biotin-peptide can bind to the cancer cells embedded in the surgical sections, the binding ability between the peptide and formalin-fixed paraffin-embedded surgical section is very weak, so almost no binding phenomenon can be observed. It is impossible to anticipate the efficacy of chemotherapy for cancer patient after surgery using this method. Currently, there is not yet a method of pathological diagnosis for targeted peptide to bind to formalin-fixed paraffin-embedded specimens in surgical sections.

SUMMARY OF THE INVENTION

The present invention provides a method of peptide histochemical diagnosis, which solves the problem to stain the tumor cells of surgical specimens fixed in formalin and embedded in paraffin sections as the relationship between antibody and antigen. In other words, before peptide-targeted chemotherapy is applied to the patients with cancer, it needs to concern about the individual differences in tumor cells of the patients clinically. Prior to the targeted peptides chemotherapy, the method of the present invention is used to identify whether the targeted peptides can bind to the tumor cells of the patients, and the targeted peptides chemotherapy can be used to treat the patient if the binding phenomenon is observed.

In the one aspect, the present invention provides for peptide histochemical diagnosis, comprising: a. Providing a paraffin section of formalin-fixed tumor specimen obtained from sectioning and deparaffinzing a tumor specimen embedded in paraffin block; b. Providing a targeted peptide-dextran coated iron oxide nanoparticle, the surface of the iron oxide nanoparticle is coated with dextran, a N-terminus of the targeted peptide is linked to the dextran; and c. Incubating the paraffin section of tumor specimen (after retrieval of binding protein) with the targeted peptide-dextran coated iron oxide nanoparticle, then staining with a reagent to reveal a specific color, wherein a tumor cell in the paraffin section of tumor specimen reveals the specific color, and a normal cell in the paraffin section of tumor specimen is not stained; the reagent is Prussian blue reagent, the specific color of Prussian blue reagent reacting with the targeted peptide-dextran coated iron oxide nanoparticles is blue.

In the present invention, the paraffin section of tumor specimen is embedded in paraffin wax after being formalin-fixed and dehydrated. In addition, the tumor specimen further processes a high-pressure treatment (for retrieval of binding protein) to obtain the paraffin section of tumor specimen after deparaffinization.

In the present invention, the targeted peptide-dextran coated iron oxide nanoparticles are synthesized by at least 10 targeted peptides linked to dextran coated iron oxide nanoparticle, and the targeted peptide of the targeted peptide-dextran coated iron oxide nanoparticles binds to the tumor cells.

In the present invention, the tumor is nasopharyngeal carcinoma (NPC), breast cancer, hepatoma, pancreatic cancer, non-small cell lung cancer (NSCLC) or neuroblastoma.

In another aspect, the present invention also provides a method of a targeted peptide-dextran coated iron oxide nanoparticle for detecting the peptide binding protein in a paraffin section of tumor specimen, wherein a normal cell in the paraffin section of tumor specimen is not stained, the paraffin section of tumor specimen reveals a color if a tumor cell in the paraffin section of tumor specimen bound by the targeted peptide-dextran coated iron oxide nanoparticle.

In another aspect, the present invention further provides a method of reducing the side effects of cancer chemotherapy by using peptides, comprising: administering to a subject suffering from a cancer an effective amount of a chemotherapeutic drug and peptides, wherein the peptides are at least two selected from the group consisting of amino acid sequences of SEQ ID NO:1, SEQ ID NO:2, and SEQ ID NO:6.

In another aspect, the present invention further provides a method of reducing the side effects of cancer chemotherapy by using peptide, comprising: administering to a subject suffering from a cancer an effective amount of a first set comprising a first chemotherapeutic drug and a first peptide, and a second set comprising a second chemotherapeutic drug and a second peptide, wherein each the first peptide and the second peptide is selected from the group consisting of amino acid sequences of SEQ ID NO:1, SEQ ID NO:2, and SEQ ID NO:6, wherein the second set is administered a period of time after the first set.

Peptide histochemical diagnosis of the present invention, which comprises to use a targeted peptide-dextran coated iron oxide nanoparticle, the N-terminus of the targeted peptide is linked to dextran, and each targeted peptide-dextran coated iron oxide nanoparticle can link to at least 10 targeted peptides; the C-terminus of the targeted peptide of the targeted peptide-dextran coated iron oxide nanoparticle can bind to the tumor cells. Therefore, when the targeted peptide-dextran coated iron oxide nanoparticle of the present invention used to react with paraffin section of tumor specimen, 10 targeted peptides can bind to the tumor cells. The targeted peptide-dextran coated iron oxide nanoparticle of the present invention can reveal blue color after iron oxide nanoparticles reacting with Prussian blue reagent, and the reaction product precipitates in the tumor cells bound by the targeted peptides but not in the cytoplasm of the normal epithelial cells or fibroblasts, and a little reaction products are seen in the membrane of the tumor cells. In summary, the reaction products present in the tumor cells rather than normal cells, although normal cells may show very little of the targeted protein in its cytoplasm (the mononuclear cells may show a little more) but not show in their membranes.

The targeted peptide in the present invention is the short sequence having only 12 amino acids, and the targeted peptides are small molecular compared to the antibody, therefore, after binding to the nanoparticales, the short sequence peptide still have a tiny volume, so the targeted peptide-linked dextran-coated iron oxide nanoparticles can be allowed to enter into the extracellular space. Additionally, one nanoparticle can be linked by many short sequence peptides, which allows more binding ability for targeting tumor cells.

Thus, prior to apply the targeted peptide chemotherapy to treat a cancer patient, peptide histochemical diagnosis of the present invention can be used to identify whether the targeted peptides can bind to a paraffin section of tumor specimen of the patients, and then the targeted peptide chemotherapy can directly be used to treat the patient if the binding phenomenon is observed, which makes therapy effectively.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Definition

Figure 1:
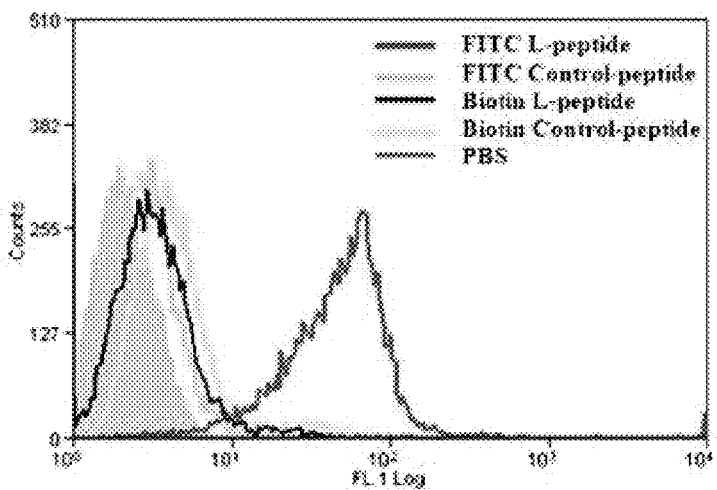
FIG. 1 is a graph depicting flow cytometry analysis of FITC (Fluorescein isothiocyanate)-targeted peptide SEQ ID NO: 1 binding to the nasopharyngeal carcinoma (NPC)-TW07 and other cancer cell lines. Portion A of FIG. 1 shows a strong binding activity of the targeted peptide SEQ ID NO: 1 to NPC cells. The NPC cells incubated with PBS (phosphate buffered saline) are used as a negative control. The FITC-linked control peptide SEQ ID NO: 3 and the biotin-linked targeted peptide SEQ ID NO: 1 or biotin-linked the control peptide all shows very weak binding activity. Portion B of FIG. 1 is the flow cytometry analysis of the FITC-targeted peptide SEQ ID NO:1 binding to various cancer cell lines but not immortalized cell line. The peaks shown from left to right are human immortalized embryonic renal cells (239T), NPC-TW01, non-small cell lung cancer (A549), breast cancer (MB157), neuroblastoma (Be2C), NPC-TW07 and non-small cell lung cancer (H1299) cell lines. All shows a clear binding peak except the immortalized embryonic renal cell line (293T) without showing any binding phenomenon.
Figure 1:
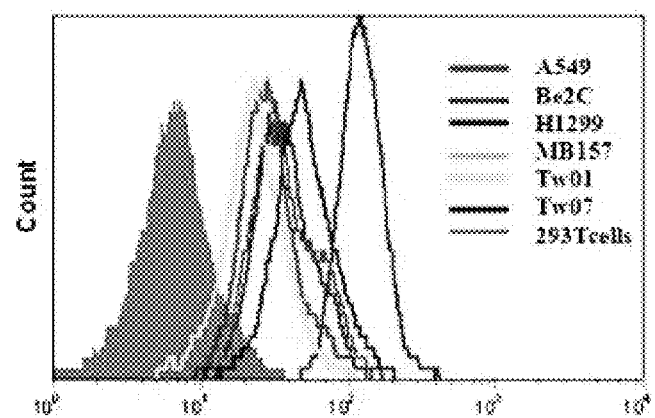

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention.

Unless otherwise defined, all technical and scientific terms used herein have the same meaning as commonly understood by one of ordinary skill in the art to which this invention pertains. In the case of conflict, the present document, including definitions will be explained clearly.

As used herein, "targeted peptide" shall generally mean a peptide that binds to a cancer cell but does not bind to a normal cell.

As used herein, "approximately" shall generally mean within 20 percent, preferably within 10 percent, and more preferably within 5 percent of a given value or range. Numerical quantities given herein are approximate, meaning that the term "approximately" can be inferred if not expressly stated.

As used herein, the term "chemotherapy drug" refers to carboplatin, cisplatin, oxaliplatin, cyclophosphamide, dacarbazine, temozolomide, gemcitabine, capecitabine, cladribine, clofarabine, cytarabine, floxuridine, fludarabine, hydroxyurea, methotrexate, pemetrexed, pentostatin, thioguanadine, daunorubicin, doxurubicin, epirubicin, idarubicin, topotecan, irinotecan, etoposide, eniposide, colchicine, vincristine, vinblastine, vinorelbine, paclitaxel, and docetaxel.

Preparation of Cell Lines, Biopsy and Surgical Specimens and Peptides

Cell lines: Cell lines used here include nasopharyngeal carcinoma (NPC-TW01, NPC-TW06 and NPC-TW07), breast cancer (MDA-MB231 and MB157), non-small cell lung cancer (H1299 and A549), neuroblastoma (Be2C), hepatoma (Hep G2), pancreatic cancer (Pan 1) cell lines and immortalized embryonic renal epithelia (TEKID) (293T): all cell lines were cultured in the DMEM containing L-glutamine and 10% fecal calf serum and incubated in the 10% $CO_2$ incubator as routine cell culture condition.

Biopsy and surgical specimens: The biopsy specimens and surgical specimens of nasopharyngeal carcinoma, breast cancer, hepatoma and pancreatic cancer are obtained from the archives of the Department of Pathology at the National Taiwan University Hospital (NTUH) with the approval for usage by NTUH Institution Review Board (IRB).

Peptide: Peptides include: (1) targeted peptide SEQ ID NO:1 and SEQ ID NO:2; (2) control peptide SEQ ID NO:3; (3) FITC (Fluorescein isothiocyanate)-targeted peptide SEQ ID NO:1; (4) FITC-control peptide; (5) biotin-targeted peptide SEQ ID NO:1 (B-P); (6) biotin-control peptide (B-C-P); (7) biotin-5 amino acids spacer-targeted peptide SEQ ID NO:1, i.e. biotin-modified-peptide (B-m-P), wherein the sequence of 5 amino acids spacer is SEQ ID NO:4; (8) targeted peptide SEQ ID NO:1-linked dextran-coated iron oxide nanoparticles (P-Dex-$Fe_3O_4$); and (9) control peptide-linked dextran-coated iron oxide nanoparticles (CP-Dex-$Fe_3O_4$). Most of the peptides are synthesized by GeneDiveX, Inc, (Las Vegas, U.S.A.), and Dex-$Fe_3O_4$ is purchased from a commercial source (MagQu Co., Ltd., Taipei, Taiwan).

Example 1: Synthesis and Characterization of Magnetic Nanoparticles

The dextran coated-$Fe_3O_4$ is linked with the targeted peptide SEQ ID NO:1 or the FITC-targeted peptide SEQ ID NO:1 by the MagQu Company. Dextran is used as the hydrophilic surfactant layer. The iron oxide fluid with the desired concentration is available by diluting the highly concentrated iron oxide fluid with a pH 7.4 phosphate buffered saline (PBS) solution. For iron oxide labeling, the NPC-TW01 cells are cultured for 24 hr, incubated with or without the targeted peptide SEQ ID NO:1-linked dextran-coated iron oxide nanoparticle (P-Dex-$Fe_3O_4$) at a concentration of 10 µg $Fe_3O_4$/mL in the incubation media for 1 hr at 4° C. and incubated for 4 hr at 37° C. in a 10% $CO_2$ incubator. Cells are washed in a 2% fetal bovine serum in PBS. After fixation, the binding ability between the targeted peptide SEQ ID NO: 1 and tumor cells can be observed by Prussian blue reagent; each iron oxide nanoparticle is bound by approximately above 10 targeted peptides.

Example 2: Flow Cytometry Analysis of the Targeted Peptide SEQ ID NO: 1 Binding Cells in Different Cell Lines The cultured cells, including nasopharyngeal carcinoma (NPC-TW01 and NPC-TW07), non-small cell lung cancer (H1299 and A549), neuroblastoma (Be2C), breast cancer (MB157) and immortalized embryonic renal epithelia (TEKID) (239T) are subjected to flow cytometer (FACSCAN, BD Co., U.S.A.) after the FITC (Fluorescein isothiocyanate)-targeted peptide SEQ ID NO:1 treatment. Simultaneously, FITC-control peptide, FITC-biotin-targeted peptide SEQ ID NO: 1 (B-P) and FITC-biotin-control peptide (B-C-P) are used for flow cytometry comparison.

When NPC-TW07 cells are incubated with FITC-targeted peptide SEQ ID NO: 1, a clear peak is found in the histogram (portion A of FIG. 1). When the targeted peptide SEQ ID NO: 1 is linked with biotin, very weak or no binding is seen. When other NPC cell line, such as NPC-TW01, and other cancer lines including non-small cell lung cancer (A549 and H1299), neuroblastoma (Be2C) and breast cancer (MB157) are incubated with the FITC-targeted peptide SEQ ID NO:1, as shown in portion B of FIG. 1, all shows a clear binding peak except the immortalized renal cell line (293T) without showing any binding phenomenon.

Example 3: Localization of the Targeted Peptide SEQ ID NO: 1 in Nasopharyngeal Carcinoma Because the targeted peptide SEQ ID NO:1 binds weakly to the cancer cells after conjugating to biotin, the sequence of this peptide was modified as Biotin-modified-peptide (B-m-P). B-m-P is modified by adding 5 amino acids spacer SEQ ID NO: 4 to N-terminus and linking with biotin. B-m-P can bind to the small surgical NPC specimens, but the result is not good enough to observe a clear reaction product. For more than 1 cm in diameter of the surgical specimens, B-m-P still can not bind to the surgical specimens, there is no binding phenomenon can be observed, while the targeted peptide SEQ ID NO:1-linked dextran-coated iron oxide nanoparticles (P-Dex-$Fe_3O_4$) of the present invention can bind to tumor cells and be stained with Prussian blue reagent. The result is excellent so as to name "peptide histochemical diagnosis".

In the present invention, P-Dex-$Fe_3O_4$ has to be prepared at first. The nanoparticle (MW 60,000 to 70,000) is composed of an iron oxide core coated with dextran polymer. Each dextran-coated iron oxide nanoparticles can be linked with more than 10 targeted peptides.

Figure 2:
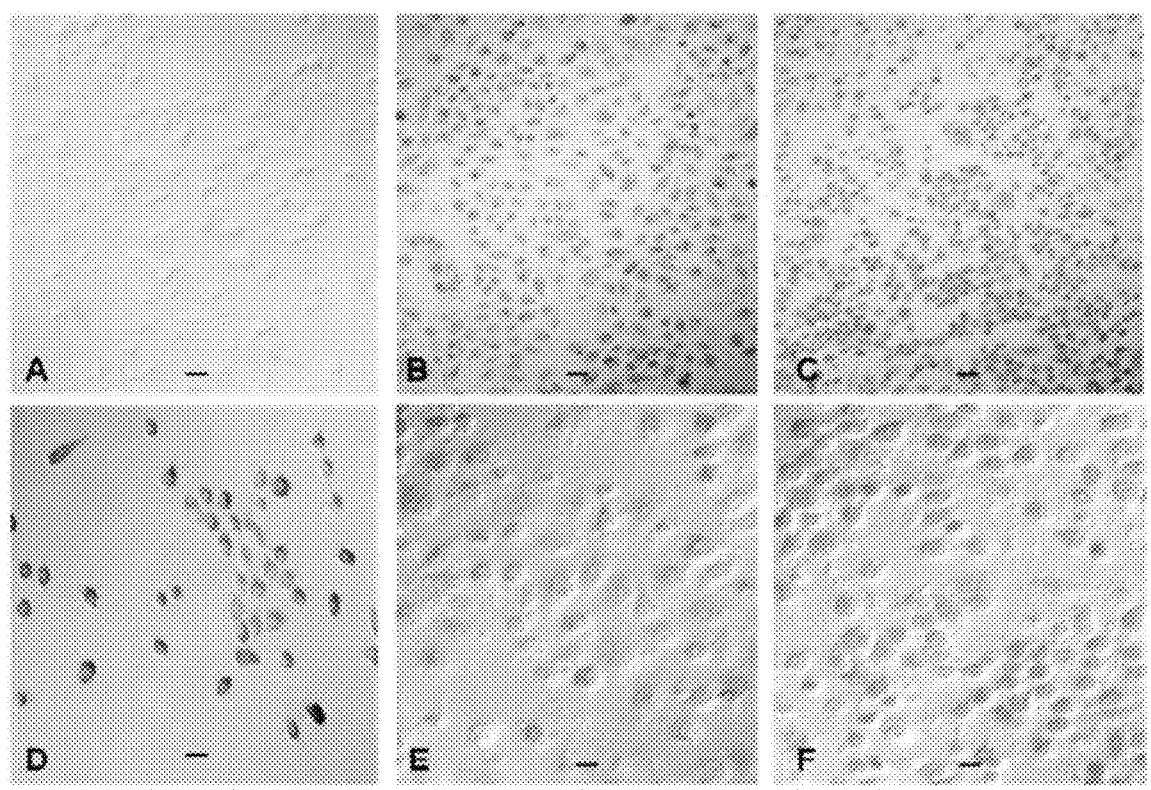
FIG. 2 is the image of localization of the targeted peptide binding protein in nasopharyngeal carcinoma (NPC) cells by incubation of detergent permealized formalin-fixed NPC cells incubated with biotin linked control peptide (portion A of FIG. 2) and biotin linked targeted peptide (portion B of FIG. 2), and are visualized by Avidin-biotin peroxidase complex and peroxidase substrate diaminobenzidine (DAB). The NPC tumor cells show DAB reaction product in most of tumor cell cytoplasm (portion D of FIG. 2) but not in the control peptide treated cells (portion A of FIG. 2). Portions B to F of FIG. 2 are the images of localization of the targeted peptide SEQ ID NO: 1 binding protein in NPC cell; the control peptide is SEQ ID NO: 3; portions B and E of FIG. 2 are the images of the targeted peptide SEQ ID NO: 1-linked dextran-coated iron oxide nanoparticles (P-Dex-$Fe_3O_4$) incubated with NPC cell lines and stained with Prussian blue reagent, and the tumor cells reveal Prussian blue reaction products. Portion E of FIG. 2 is a high magnification of portion B of FIG. 2. Portion C of FIG. 2 is the image of control peptide-linked dextran-coated iron oxide nanoparticles (CP-Dex-$Fe_3O_4$) and reveals some non-specific reaction product attached to a few tumor cells. Portion F of FIG. 2 is a high magnification of portion C of FIG. 2.

FIG. 2 shows the results of targeted peptide SEQ ID NO:1 binding to NPC cells (NPC-TW01): when the NPC cultured cells are also incubated with P-Dex-$Fe_3O_4$ nanoparticles at 4° C. for 1.0 hr and 37° C. for 4 hr, and fixed for reacting with Prussian blue reagent, the reaction products are seen in the cytoplasm of a majority of the tumor cells (portions B and E of FIG. 2); however, the tumor cells treated with CP-Dex-$Fe_3O_4$ reveals no specific reaction product (portions C and F of FIG. 2). If the tumor cells are fixed and permeabilized by protease at first, then incubated with P-Dex-Fe$_3$O$_4$, and subjected to avidin-biotin-peroxidase complex and peroxidase treatment, the brown reaction product can be seen in most of the tumor cells (portion A of FIG. 2) but not in the control peptide treated case (portion A of FIG. 2).

Example 4: Localization of the Targeted Peptide SEQ ID NO: 1 in Breast Cancer

Figure 3:
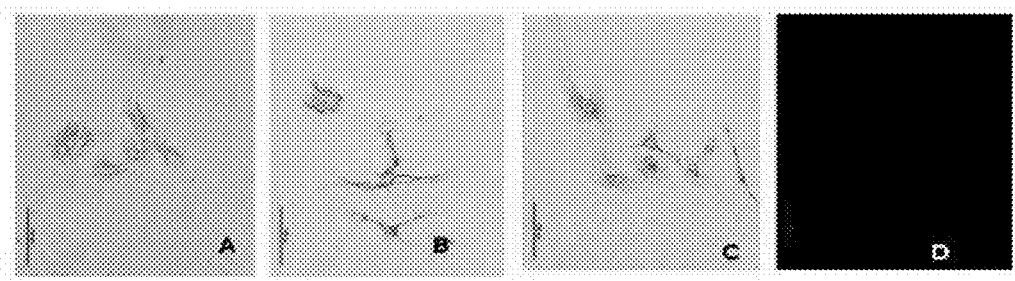
FIG. 3 is the image of Prussian blue staining for breast cancer cell line (MDA-MB-231) treated with dextran-coated iron oxide nanoparticles (Dex-$Fe_3O_4$), the targeted peptide SEQ ID NO:1-linked dextran-coated iron oxide nanoparticles (P-Dex-$Fe_3O_4$) and FITC-targeted peptide SEQ ID NO:1-linked dextran-coated iron oxide nanoparticles (FITC-P-Dex-$Fe_3O_4$). Portion A of FIG. 3 is breast cancer cells incubated with Dex-$Fe_3O_4$, C is cancer cells treated with P-Dex-$Fe_3O_4$, portions B and D of FIG. 3 are cancer cells treated with FITC-P-Dex-$Fe_3O_4$. Portion A of FIG. 3 shows no reaction product. Portions B and C of FIG. 3 show blue reaction product in the cytoplasm of breast cancer cells. Portion D of FIG. 3 shows the fluorescent signal in the tumor cells as blue reaction product shown in portion B of FIG. 3. Bar in each panel=100 μm.

FIG. 3 shows the results of targeted peptide SEQ ID NO:1 binding to breast cancer cells (MDA-MB-231): P-Dex-Fe$_3$O$_4$ of the present invention and FITC (Fluorescein isothiocyanate)-targeted peptide SEQ ID NO:1-linked dextran-coated iron oxide nanoparticle (FITC-P-Dex-Fe$_3$O$_4$) treated breast cancer cells, respectively, results show that the reaction products appear in most of the cytoplasm of breast cancer cells (portion C of FIG. 3), while no reaction product is seen in the control cells treated with Dex-Fe$_3$O$_4$ (portion A of FIG. 3). In FITC-L-P-Dex-Fe$_3$O$_4$ nanoparticles treated cells, reaction products are seen in the cytoplasm of breast cancer cells (portion B of FIG. 3), and the fluorescent signal is also seen in the same tumor cells (portion D of FIG.).

Figure 4:
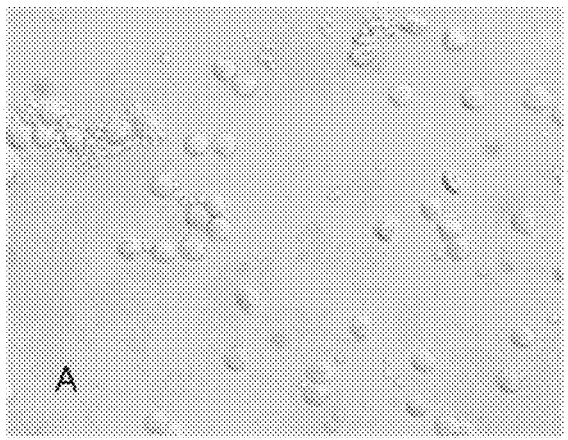
FIG. 4 is the image of Prussian blue staining for blood monocytes, hepatoma (Huh 7) and pancreatic cancer cell line (Pan 1) treated with P-Dex-$Fe_3O_4$ for 1 hr at 4° C. and 4 hr at 37° C. and fixed for Prussian blue reaction; the targeted sequence is SEQ ID NO:1. Portions A and B of FIG. 4 show no blue reaction product in blood monocytes. Portion A of FIG. 4 is the control panel of portion C of FIG. 4, and portion B of FIG. 4 is the control panel of portion D of FIG. 4. Portions A and B of FIG. 4 all show that P-Dex-$Fe_3O_4$ do not bind to normal blood cells. Portions C and D of FIG. 4 show blue reaction product in hepatoma and pancreatic cancer cell lines, respectively.
Figure 4:
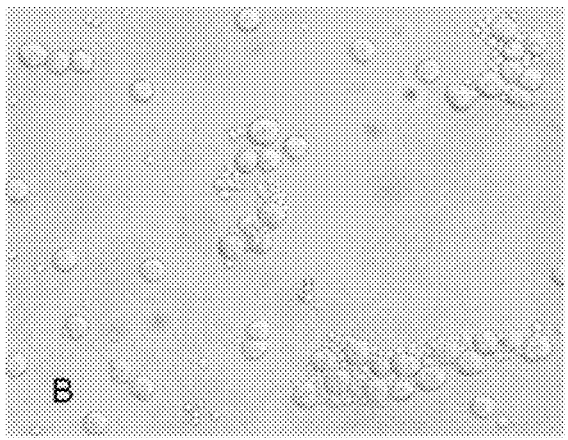
Figure 4:
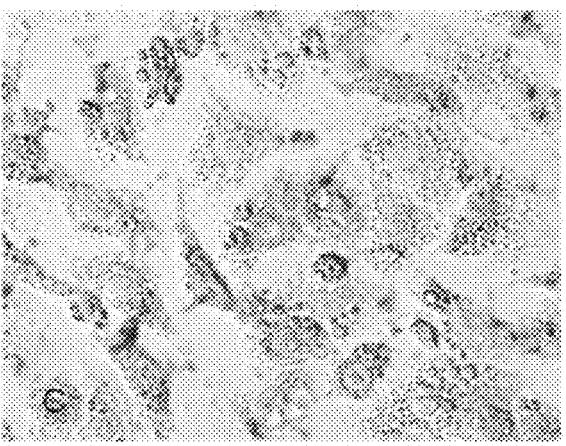
Figure 4:
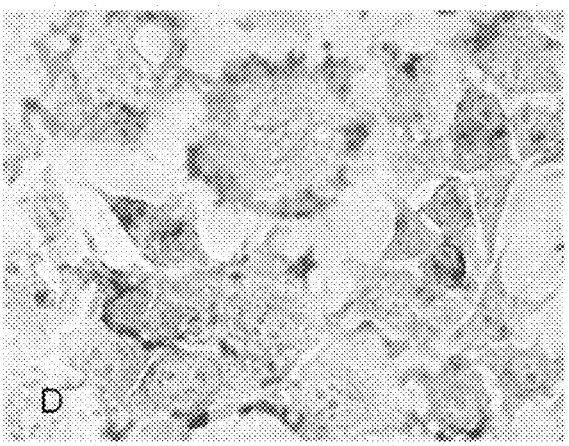

Example 5: Localization of the Targeted Peptide SEQ ID NO: 1 in Blood Monocytes, Hepatoma and Pancreatic Cancer Cells Blood monocytes, hepatoma (Hep G2) and pancreatic cancer (Pan 1) cell lines are incubated with P-Dex-Fe$_3$O$_4$ nanoparticle for 1.0 hr and 37° C. for 4 hr, and then are stained with Prussian blue reagent. As shown in portions C and D of FIG. 4, hepatoma (Hep G2) and pancreatic cancer (Pan 1) cell lines show blue reaction products. But blood monocytes show no reaction product (portions A and B of FIG. 4); these results indicate that the protein bound by the targeted peptide SEQ ID NO: 1 is expressed in cancer cells but not in blood monocytes.

Example 6: Localization of the Targeted Peptide SEQ ID NO: 2 in Hepatoma Cells

Figure 5:
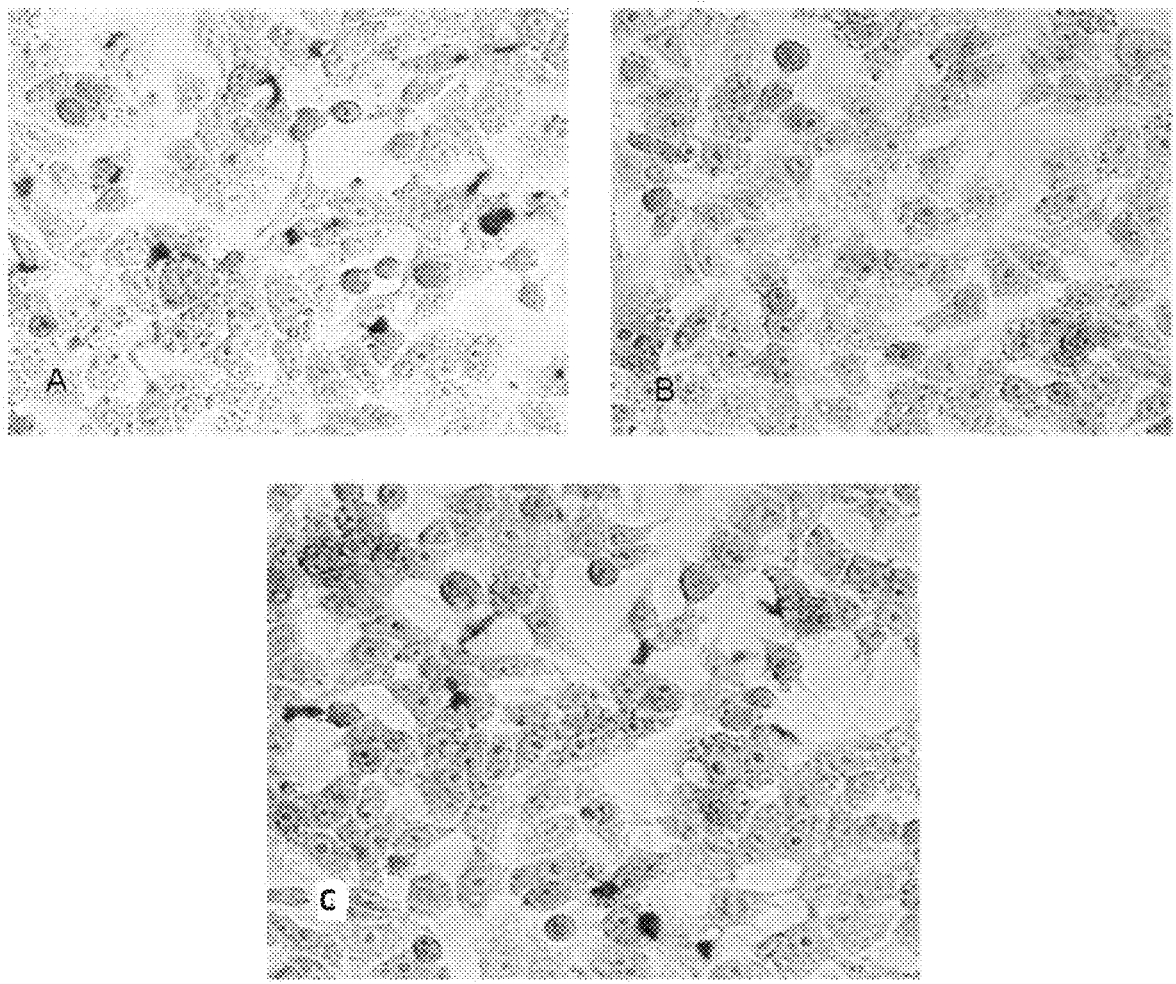
FIG. 5 is the image of Prussian blue staining for hepatoma cell lines (Hep G2) treated with the targeted peptide. Portion A of FIG. 5, the targeted sequence is SEQ ID NO: 1, portion C of FIG. 5, the targeted sequence is SEQ ID NO: 2. Portions A and C of FIG. 5 show blue reaction products of the targeted peptide SEQ ID NO:1-linked dextran-coated iron oxide nanoparticles and the targeted peptide SEQ ID NO:2-linked dextran-coated iron oxide nanoparticles binding to hepatoma cell lines (Hep G2) separately; portion B of FIG. 5 shows the control iron oxide nanoparticle not binding to hepatoma cell line (Hep G2).

In addition to the targeted peptide SEQ ID NO: 1, the present invention also provides another targeted peptide SEQ ID NO: 2 for synthesizing the targeted peptide SEQ ID NO: 2-linked dextran-coated iron oxide nanoparticles. Hepatoma cell lines (Hep G2) are incubated with the targeted peptide SEQ ID NO: 1-linked dextran-coated iron oxide nanoparticles and the targeted peptide SEQ ID NO: 2-linked dextran-coated iron oxide nanoparticle, respectively, then are reacted with Prussian blue reagent. As shown in portions A and C of FIG. 5, the targeted peptide SEQ ID NO:1-linked dextran-coated iron oxide nanoparticles and the targeted peptide SEQ ID NO:2-linked dextran-coated iron oxide nanoparticles all show blue reaction product, the hepatoma cell lines treated with control peptide-linked dextran-coated iron oxide nanoparticle (CP-Dex-Fe$_3$O$_4$) reveals no specific reaction product (portion B of FIG. 5).

In view of abovementioned examples, as long as a targeted peptide can be used to bind to a type of cancer cells, the targeted peptide can be used to bind to cancer cells in surgical paraffin section of the same cancers by using the method of the present invention.

Example 7: Localization of the Targeted Peptide SEQ ID NO: 1 in Nasopharyngeal Carcinoma (NPC) Biopsy Specimens The NPC biopsy specimens are fixed in formalin and embedded in paraffin block then are cut into thin sections with 5 mm After deparaffinizaion, the paraffin-embedded sections are retrieved the binding capability of targeted peptide binding protein with Trilogy (Cell Marque, Rocklin, Calif.), then autoclaved to 132° C.-140° C. for 5-10 min and cooled to room temperature. The sections are incubated overnight at 4° C. with the P-Dex-Fe$_3$O$_4$ nanoparticles, and washed with PBS, then are incubated for 15-30 min with routine Prussian blue reagent (containing 2% potassium ferricyanide (Sigma-aldrich.com. St Louis Mo., U.S.A.) and 0.5 N HCl in dH$_2$O=1:1), followed by counterstaining for 5 min with nuclear fast red solution, washed with water, and mounted with 50% glycerol directly or with balsam after alcohol dehydration.

In the present invention, peptide histochemical diagnosis can be applied not only to cancer cell lines but also to paraffin-embedded cancer sections fixed in formalin Therefore the peptide histochemical diagnosis of the present invention can be applied to any cancer type section.

Figure 6:
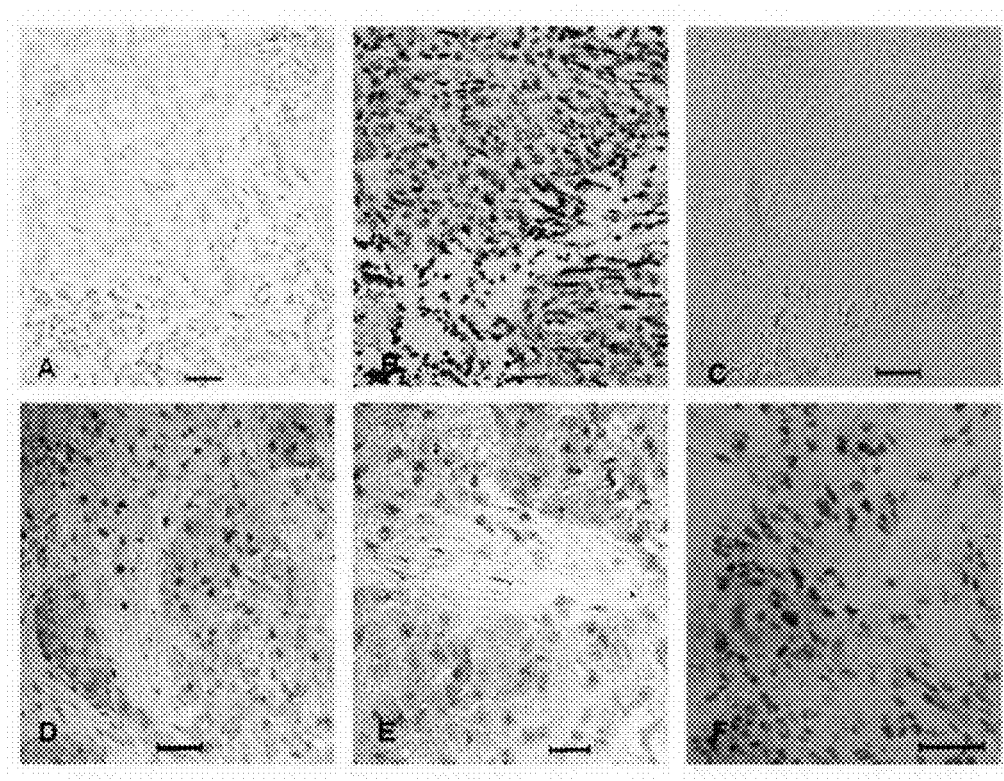
FIG. 6 is the image of peptide histochemical localization of peptide targeted protein in NPC biopsy specimens. A and C are the images of NPC biopsy specimens treated with the control peptide (SEQ ID NO: 3-Dex-Fe$_3$O$_4$). Portions A, B, D and E of FIG. 6 are the images of NPC biopsy specimens counterstained with nuclear fast red. Portions C and F of FIG. 6 show the images of NPC biopsy specimens without counterstaining with nuclear fast red. Portions B, D, E and F of FIG. 6 show the binding results of targeted peptide SEQ ID NO: 1-linked dextran-coated iron oxide nanoparticle (P-Dex-Fe$_3$O$_4$) in NPC biopsy specimens from different NPC patients. Portions B, D and E of FIG. 6 are the images stained by Prussian blue reagent and counterstained with nuclear fast red. F is the image only stained by Prussian blue reagent. In tumor nests, there are Prussian blue reaction products in most NPC biopsy specimens (B, D, E and F). Portions B, D and E of FIG. 6 show clear staining of infiltrating tumor cells in stromal regions. Bar in each panel=25 μm.

The results show binding capability of the targeted peptide SEQ ID NO: 1 in NPC biopsy specimens. Because the Biotin-modified-peptide (B-m-P) does not bind easily to the formalin-fixed paraffin-embedded tissue section, the present invention provides a method for peptide histochemical diagnosis, in one embodiment, which uses targeted peptide SEQ ID NO: 1-linked dextran-coated iron oxide nanoparticle (P-Dex-Fe$_3$O$_4$) binding to NPC cells. The results show that the Prussian blue reaction product is easily identified in the tumor cells of stained sections (portions B, D, E and F of FIG. 6). Some tumor cells having infiltrated stromal region also reveal reaction products (portions B, D and E of FIG. 6). The tumor cells in the tumor nests of NPC biopsy specimens reveal positive reaction products; however, the tumor cells treated with CP-Dex-Fe$_3$O$_4$ show no staining (portions A and C of FIG. 6). portion A of FIG. 6 is counterstained with nuclear fast red; portions C and F of FIG. 6 are without counterstaining with nuclear fast red.

Example 8: Localization of the Targeted Peptide SEQ ID NO: 1 in Breast Cancer Surgical Specimens In the present invention, peptide histochemical diagnosis can be applied to formalin-fixed paraffin-embedded breast cancer sections.

The results show binding capability of the targeted peptide SEQ ID NO: 1 in breast surgical specimens. When biotin-modified-peptide (B-m-P) is used to bind to the formalin-fixed paraffin-embedded tissue sections, a very weak or no binding signal can be obtained after staining (figure no show). The result indicates that the biotin linked modified targeted peptide SEQ ID NO: 1 (B-m-P) can not easily bind to the formalin-fixed paraffin-embedded tissue sections.

Figure 7:
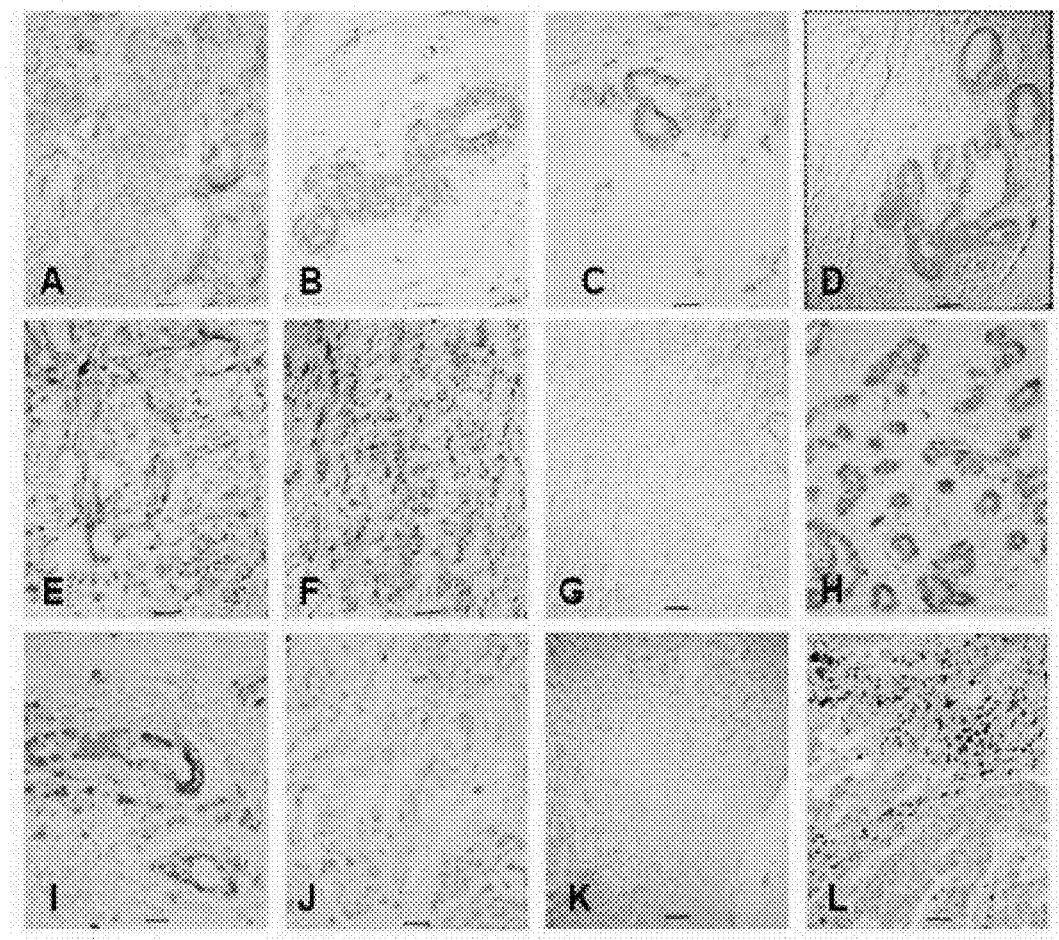
FIG. 7 is the image of peptide histochemical localization of peptide targeted protein in breast cancer surgical specimens from different patients. Portions B-F and H-L of FIG. 7 are the images of breast cancer surgical specimens treated with the targeted peptide SEQ ID NO:1-linked dextran-coated iron oxide nanoparticles (P-Dex-Fe$_3$O$_4$). Portions A and G of FIG. 7 are the images of breast cancer surgical specimens treated with control peptide-linked dextran-coated iron oxide nanoparticle (CP-Dex-Fe$_3$O$_4$) showing no Prussian blue reaction product. Portions A-F of FIG. 7 are the images stained by Prussian blue reagent and counterstained with nuclear fast red, portions G-L of FIG. 7 are the images only stained by Prussian blue reagent. Portions B-F of FIG. 7 show more or less Prussian blue reaction product in tumor cells in each breast cancer surgical section. In the stromal region, there are no reaction product in endothelial cells and fibroblasts. Portions K and L of FIG. 7 show the results of the stained breast cancer cells in the metastatic axillary lymph nodes, and the blue reaction products only reveal in the tumor cells, but not in the macrophages. In portion L of FIG. 7, there are many carbon-laden macrophages showing no blue reaction products. Bar in portions A-J of FIG. 7=25 μm; bar in portion K f FIG. 7=100 μm.

Thus, peptide histochemical diagnosis of the present invention can be applied to localization of the targeted peptide in the formalin-fixed paraffin-embedded breast cancer sections more than 1 cm in diameter of the surgical specimens. After incubation with the targeted peptide SEQ ID NO: 1-linked dextran-coated iron oxide nanoparticle (P-Dex-Fe$_3$O$_4$), the formalin-fixed paraffin-embedded breast cancer sections show the Prussian blue reaction products (portions B-F and H-J of FIG. 7), while, the stromal regions in tumor nests reveal no blue reaction product. As shown in portions K and L of FIG. 7, the tumor cells obtained from breast cancer metastatic axillary lymph nodes reveal blue reaction product. However, the breast tumor cells treated with CP-Dex-Fe$_3$O$_4$ show no staining (portions A and G of FIG. 7). In short, in breast cancer surgical specimens, the tumor cell treated with the method of present invention reveals positive reaction product.

Figure 8:
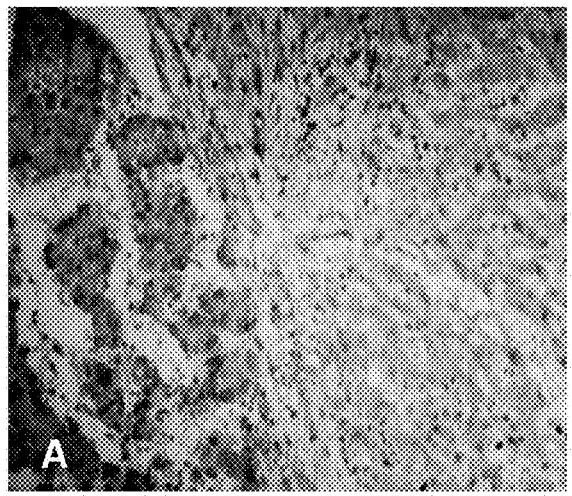
FIG. 8 is the image of peptide histochemical localization of peptide binding antigen in hepatoma surgical specimens. The surgical specimens are treated with the targeted peptide SEQ ID NO: 1-linked dextran-coated iron oxide nanoparticle (P-Dex-Fe$_3$O$_4$) (portions A and B of FIG. 8) and the targeted peptide SEQ ID NO: 2-linked dextran-coated iron oxide nanoparticle, respectively (portion C of FIG. 8). In the right part of portion A of FIG. 8, the normal cells are compressed by tumor cells, and the blue reaction products do not show in the normal cells, but show in single infiltrating tumor cells. Portion B of FIG. 8 shows a high magnification of hepatoma cells stained by reaction product. Portion C of FIG. 8 is the image of staining hepatoma surgical specimens treated with the targeted peptide SEQ ID NO: 2-linked dextran-coated iron oxide nanoparticles. Portion D of FIG. 8 is the image of staining hepatoma surgical specimens treated with the control panel (CP-Dex-Fe$_3$O$_4$); no reaction product can be seen.
Figure 8:
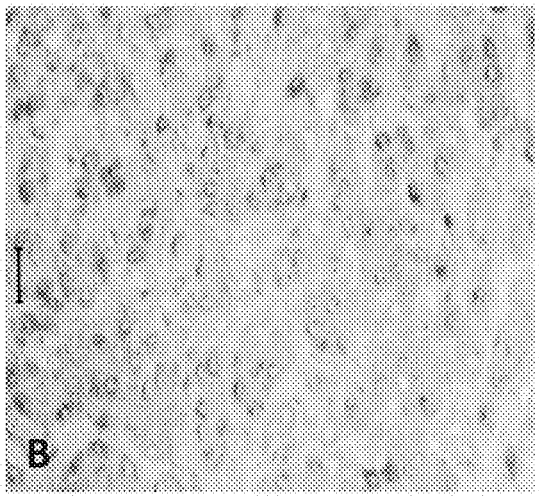
Figure 8:
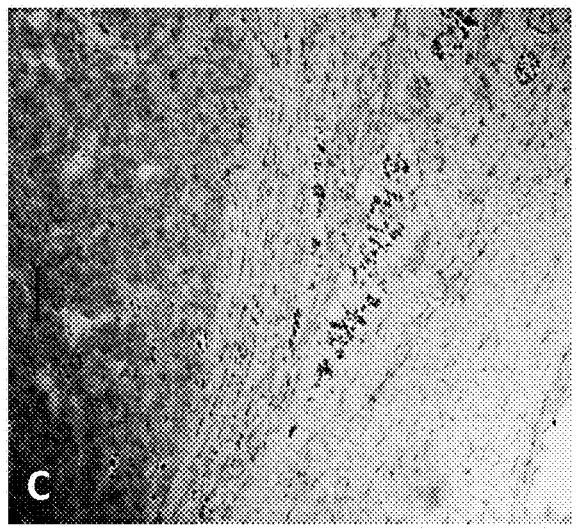
Figure 8:
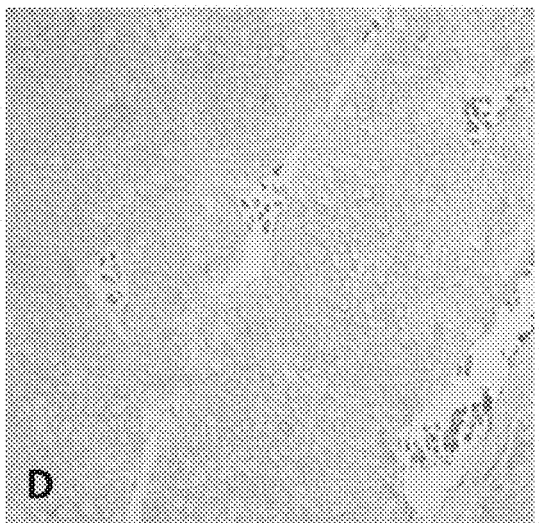

Example 9: Localization of the Targeted Peptide SEQ ID NO: 1 in Hepatoma Surgical Specimens Peptide histochemical diagnosis of the present invention can be applied to hepatoma surgical specimens. Using peptide histochemical technique, the targeted peptide SEQ ID NO: 1-linked dextran-coated iron oxide nanoparticles (P-Dex-Fe$_3$O$_4$) are used to bind formalin-fixed paraffin-embedded hepatoma sections (portion A and B of FIG. 8). Portion C of FIG. 8 shows reaction products of the targeted peptide SEQ ID NO: 2-linked dextran-coated iron oxide nanoparticles binding to hepatoma sections and the Prussian blue products can also be observed in the tumor cells. Portion D of FIG. 8 is hepatoma cells treated with CP-Dex-Fe$_3$O$_4$ and shows no reaction products.

Figure 9:
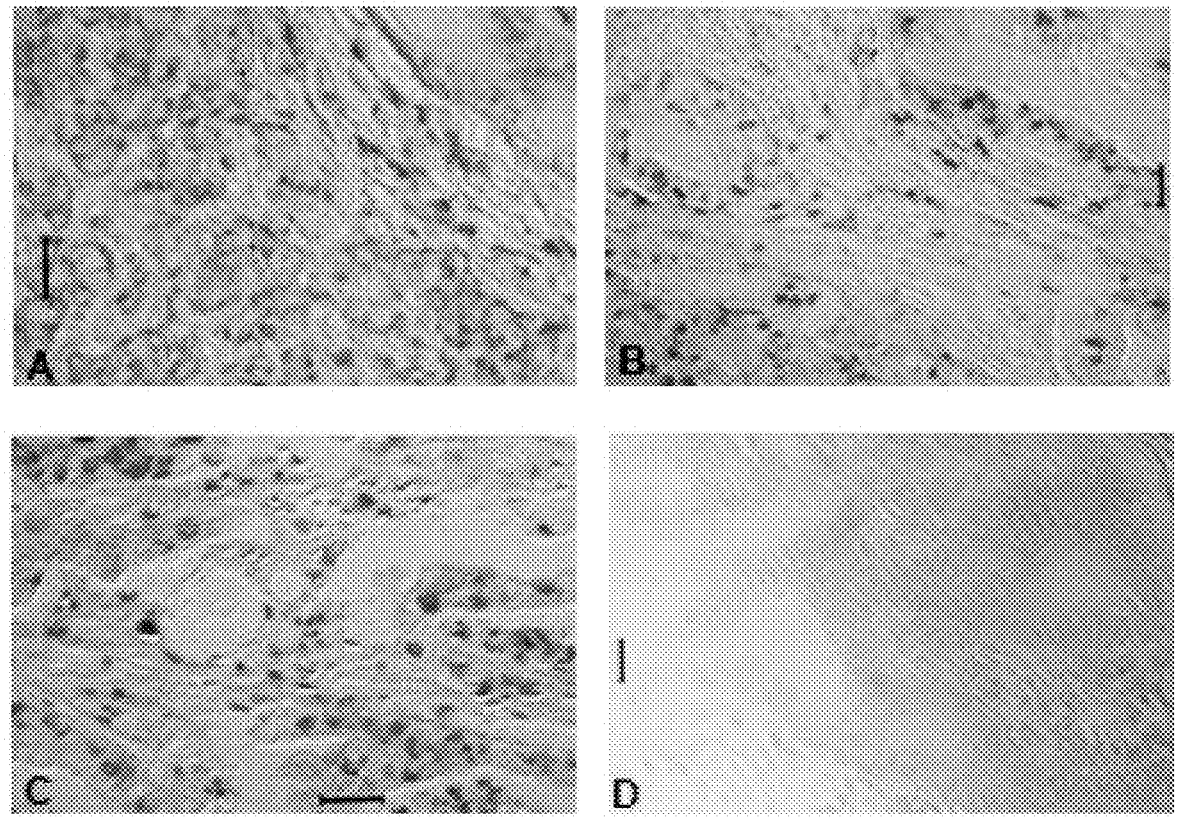
FIG. 9 is the image of peptide histochemical localization of peptide binding protein in pancreatic surgical specimens: pancreatic surgical specimens are treated with the targeted peptide SEQ ID NO:1-linked dextran-coated iron oxide nanoparticles (P-Dex-Fe$_3$O$_4$) (portions A and B of FIG. 9) and the targeted peptide SEQ ID NO:2-linked dextran-coated iron oxide nanoparticles (portion C of FIG. 9). Portions A-C of FIG. 9 all show blue reaction products. Portion D of FIG. 9 is the image of staining pancreatic surgical specimens treated with the control peptide (CP-Dex-Fe$_3$O$_4$), no reaction product can be seen.

Example 10: Localization of the Targeted Peptide SEQ ID NO: 1 and 2 in Pancreatic Surgical Specimens Peptide histochemical diagnosis of the present invention can be applied to pancreatic surgical specimens, ether the targeted peptide is SEQ ID NO: 1 or SEQ ID NO: 2. Using peptide histochemical method, the targeted peptide SEQ ID NO:1-linked dextran-coated iron oxide nanoparticles (P-Dex-Fe$_3$O$_4$) (portions A and C of FIG. 9) and the targeted peptide SEQ ID NO:2-linked dextran-coated iron oxide nanoparticles (portion B of FIG. 9) are used to bind formalin-fixed paraffin-embedded pancreatic cancer sections, respectively, and stained with Prussian blue reagent. Portions A, B and C of FIG. 9 all show the reaction products, and portion D of FIG. 9 is pancreatic cancer cells treated with CP-Dex-Fe$_3$O$_4$ and shows no reaction product.

In addition, peptide histochemical diagnosis of the present invention can be applied to different types of cancers, including: non-small cell lung cancer and neuroblastoma, which all reveal specific binding activity to FITC (Fluorescein isothiocyanate)-targeted peptide SEQ ID NO: 1; however, FITC-targeted peptide can not bind to the control immortalized embryonic renal epithelia (portion B of FIG. 1). FITC-targeted peptide SEQ ID NO: 2 can be used to bind to hepatoma and pancreatic cancer cells. These results show that the targeted peptide can bind to NPC and other cancer cells but not bind to untransformed cells.

Another aspect of the present invention, adding a large amount dosage of the targeted peptide SEQ ID NO: 1 (such as 1 mg/mL) to the NPC cells culture medium is found no any specific change of tumor cell morphology and behavior, even if the culture condition sustained to 10 days. Apparently, this finding indicate that the protein bound by the targeted peptide is not a receptor protein or the like thereof.

Furthermore, that using the targeted peptide SEQ ID NO: 1-linked dextran-coated iron oxide nanoparticle (P-Dex-Fe$_3$O$_4$) to bind the tumor surgical specimens in the present invention can be applied to clinical chemotherapy. The binding ability of the targeted peptide SEQ ID NO: 1 in the paraffin-embedded NPC or other cancer sections can be observed, because more the targeted peptide SEQ ID NO: 1 inserts into dextran coated iron oxide nanoparticles, it is anticipated that the binding capability is excellent. Therefore, incubation of the paraffin-embedded sections with the targeted peptide SEQ ID NO: 1-linked dextran-coated iron oxide nanoparticles (P-Dex-Fe$_3$O$_4$) and using Prussian blue reaction can observe the tumor cells. The results show that the Prussian blue reaction product can be easily identified in the tumor cells of the paraffin-embedded sections, regardless of whether it is a tumor nest or a single infiltrating tumor cell.

The targeted peptide-linked dextran-coated iron oxide nanoparticles of the present invention reveal that the targeted peptide can bind to all types of cancer cells, therefore, the targeted peptide-linked dextran-coated iron oxide nanoparticles can effectively bind to breast cancer or other cancer cell types. However, using the targeted peptide SEQ ID NO:1 linked with biotin-modified-peptide (B-m-P) in the paraffin-embedded breast cancer sections reveal very weak or no binding signal, even though the same targeted peptide SEQ ID NO:1 is used. Accordingly, peptide histochemical method of present invention is used to bind to breast cancer surgical specimens, a similar good result is obtained, and it does not only reveal breast cancer cells in surgical specimens but also in the metastatic axillary lymph nodes.

In another aspect of present invention, the other targeted peptide SEQ ID NO: 2 can be used to synthesize the targeted peptide SEQ ID NO: 2-linked dextran-coated iron oxide nanoparticles, and the good result in hepatoma or pancreatic cancer sections similar with SEQ ID NO: 1-linked dextran-coated iron oxide nanoparticles can also be observed when using the targeted peptide SEQ ID NO: 2-linked dextran-coated iron oxide nanoparticle.

In another aspect of present invention, the targeted peptide-linked dextran-coated iron oxide nanoparticles have been proven to bind to nasopharyngeal carcinoma, breast cancer, hepatoma and pancreatic cancer cells in vitro and in vivo. Furthermore, peptide-targeted chemotherapy shows a high efficacy with minimal adverse effect for treatment of undifferentiated NPC and breast cancer. These results suggest that the targeted peptide-linked dextran-coated iron oxide nanoparticles of present invention has a multifunctional potential for clinical application in localization of its targeted protein in surgical specimens, which can further be applied to verifying the possible effectiveness of chemotherapy to each patients.

Example 11: Localization of the Peptide-Targeted Protein in the Normal Peripheral Blood Cells The present invention has further identified another 2 peptides: SP-94-peptide and PC5-52-peptide, specifically binding to hepatoma (HepG2 and Huh-7) and pancreatic cancer (pan-1), and to lung cancer endothelial cells, respectively. The application of the peptide targeted chemotherapy with those peptides for hepatoma is described in the present embodiment.

Preparation of Peptides, Cell Lines, Surgical Specimens, and Animals:

the present invention used several different peptides to link liposomal iron oxide nanoparticle (L-Fe$_3$O$_4$) and liposomal doxorubicin (L-D). They are: L-peptide (SEQ ID NO: 1), obtained from nasopharyngeal carcinoma; control peptide (C-P)(SEQ ID NO: 5); SP-94-peptide (SEQ ID NO: 2)

obtained from hepatoma; PC5-52-peptide: (SEQ ID NO: 6) obtained from lung cancer endothelia; L-peptide linked dextran-coated iron oxide nanoparticle (L-P-Fe$_3$O$_4$); control-peptide-linked-dextran coated iron oxide (C-P-Fe$_3$O$_4$); L-peptide-linked liposomal doxorubicin (L-P-L-D); control-peptide linked liposomal doxorubicin (C-P-L-D); SP-94-peptide-linked-dextran coated iron oxide (SP-94-P-Fe$_3$O$_4$). L-peptide, SP-94-peptide and PC5-52-peptide were obtained from Genomics BIOSCI TECH. Co. Ltd. (Taipei, Taiwan), and the dextran-coated iron oxide (Fe$_3$O$_4$) was purchased from a commercial source (MAGQU CO., Ltd., Taipei, Taiwan).

Two hepatocellular carcinoma cell lines including HepG2, and Huh-7 cell lines, were obtained from the American Type Culture Collection. Both cell lines were cultured in the Dulbecco's modified Eagle medium (DMEM) containing 5% fetal calf serum and incubated in the 10% CO$_2$ incubator as routine cell culture condition. Thirty hepatocellular carcinoma surgical specimens were obtained from the archives of the Department of Pathology at the National Taiwan University Hospital (NTUH) with the approval for usage by NTUH IRB (#201103029RC). Severe combined immunodeficiency non-obese diabetic mice (NOD SCID mice) and NOD SCID gamma (NSG mice) were obtained from and investigated at the NTUH animal center. The use of animals was approved and regulated under the Institutional Animal Care and Use Committee in the College of Medicine, NTUH (The Number of Approval of Animal Use is: #20110058).

The present invention prepared L-peptide-linked dextran-coated iron oxide nanoparticles, such as, L-P-Fe$_3$O$_4$, SP-94-P-Fe$_3$O$_4$, PC5-52-P-Fe$_3$O$_4$ and control-peptide-Fe$_3$O$_4$ nanoparticles (C-P-Fe$_3$O$_4$). The dextran coated-Fe$_3$O$_4$ nanoparticles (Dex-Fe$_3$O$_4$) were purchased from MAGQU Company. This company conjugates L-peptide, SP-94-peptide and PC5-52-peptide, separately, to the Dex-Fe$_3$O$_4$ nanoparticles. Each Dex-Fe$_3$O$_4$ can be linked with more than 10 peptide molecules. For localization of the peptide targeted protein in HepG2 and Huh-7 cell lines, the present invention first have to check whether our peptide can also bind to the mononuclear cells in the human peripheral blood. The mononuclear cells were obtained from the normal personal blood using Histopaque-1077 solution (SIGMA, St, Louis, Mo. U.S.A).

Figure 10:
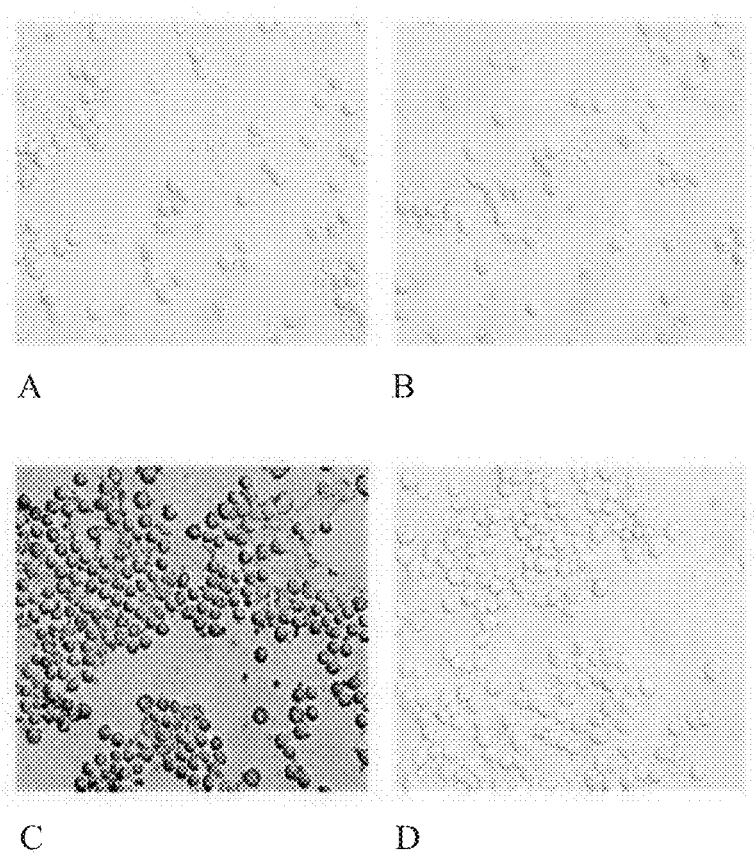
FIG. 10 is the image of Prussian blue staining for normal peripheral blood cells treated with the targeted peptide. Portion A of FIG. 10 is the image of Prussian blue staining for normal peripheral blood cells fixed in formalin and treated with L-peptide-linked dextran coated iron oxide (L-P-Fe$_3$O$_4$). Portion B of FIG. 10 is the image of Prussian blue staining for normal peripheral blood cells fixed in formalin and treated with control peptide linked dextran coated iron oxide (C-P-Fe$_3$O$_4$). Portion C of FIG. 10 is the image of Prussian blue staining for normal peripheral blood cells treated with Triton X-100 and L-P-Fe$_3$O$_4$. Portion D of FIG. 10 is the image of Prussian blue staining for normal peripheral blood cells treated with Triton X-100 and C-P-Fe$_3$O$_4$.

When the blood smears were fixed in formalin and then incubated with L-peptide-linked dextran coated iron oxide (L-P-Fe$_3$O$_4$) (portion A of FIG. 10) or control peptide linked dextran coated iron oxide (C-P-Fe$_3$O$_4$) (portion B of FIG. 10), no reaction product was seen after treated with Prussian blue reagent. If the fixed smears were treated with Triton X-100 and then incubated with L-P-Fe$_3$O$_4$, the mononuclear cells but not red blood cells showed blue reaction product in their cytoplasm (portion C of FIG. 10); however, if the C-P-Fe$_3$O$_4$ was used, no reaction product was seen in any cells (portion D of FIG. 10).

The results indicate that L-peptide cannot bind to the targeted protein on the normal blood cell membrane but can bind to the fixed and detergent treated cytoplasmic targeted protein in the normal mononuclear cells, indicating that L-peptide binding protein only presents in the cytoplasm of normal membrane cells but not on their plasma membrane.

Example 12: Localization of the Peptide-Targeted Protein in Hepatocellular Carcinoma (HCC) Cell Lines After the blood smears were fixed by formaldehyde, they were treated with or without Triton X-100 detergent and then stained with L-P-Fe$_3$O$_4$, SP-94-P-Fe$_3$O$_4$ or Control-P-Fe$_3$O$_4$ (C-P-Fe$_3$O$_4$) (40 µg/mL) and subjected to Prussian blue reaction with nuclear fast red contrast staining. Using the similar peptide histochemical procedure, the HepG2 and Huh-7 tumor cells were also stained. But in addition to the L-P-Fe$_3$O$_4$ and SP-94-P-Fe$_3$O$_4$, a ratio of 1:1 of L-P-Fe$_3$O$_4$: SP-94-P-Fe$_3$O$_4$ were mixed and used to stain the HepG2 and Huh-7 tumor cells.

Figure 11:
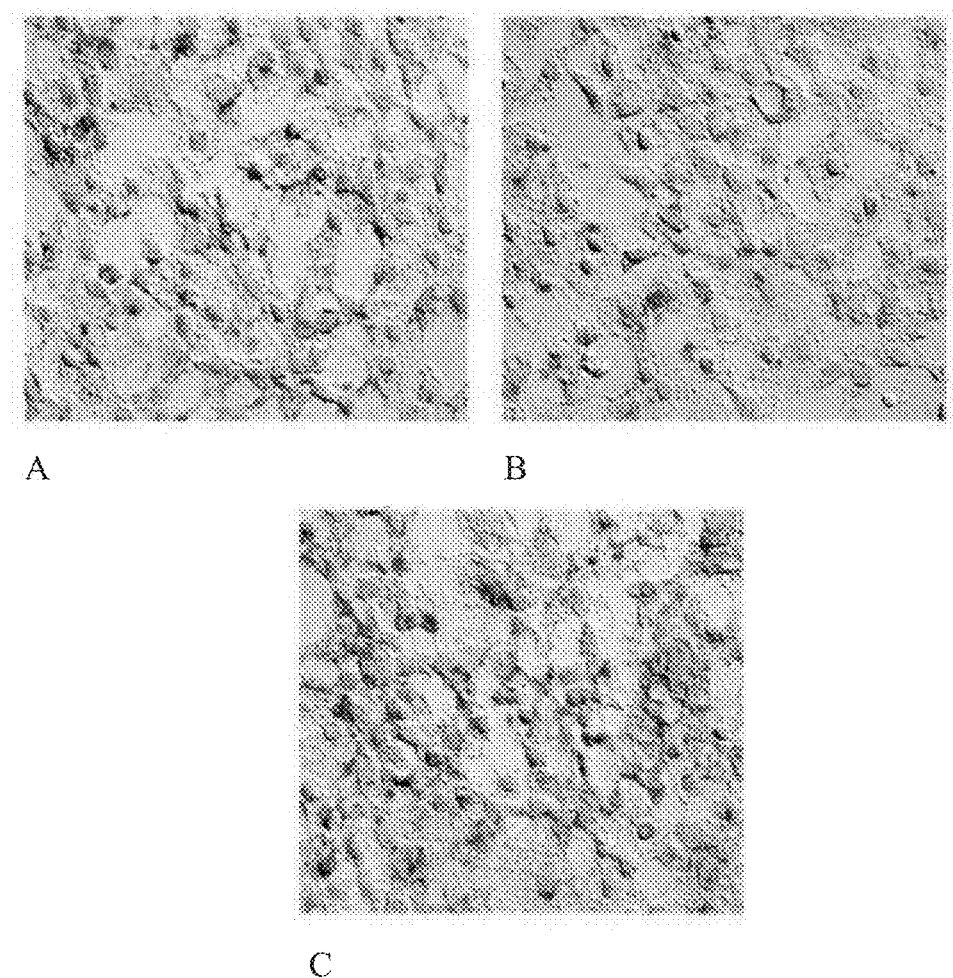
FIG. 11 is the image of Prussian blue staining for HepG2 tumor cells treated with the targeted peptide; portion A of FIG. 11, the targeted peptide is L-P-Fe$_3$O$_4$; portion B of FIG. 11, the targeted peptide is SP-94-P-Fe$_3$O$_4$; portion C of FIG. 11, the targeted peptide is a combination of L-P-Fe$_3$O$_4$ and SP-94-P-Fe$_3$O$_4$ with 1:1 ratio.
Figure 12:
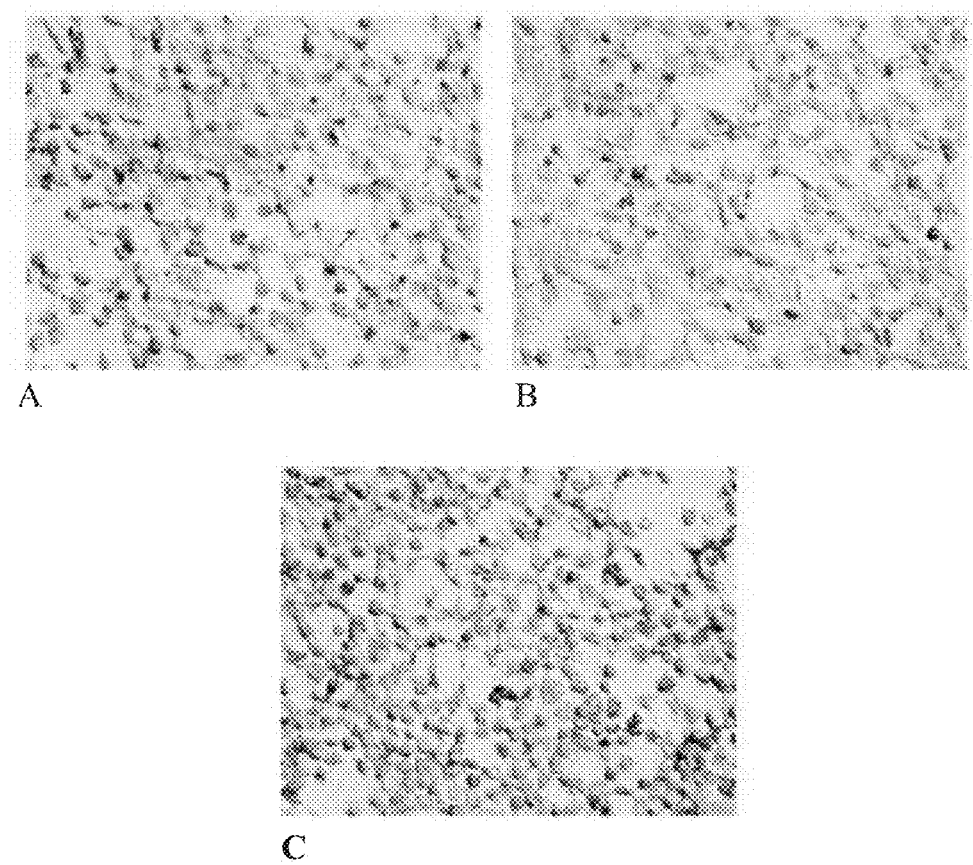
FIG. 12 is the image of Prussian blue staining for Huh-7 tumor cells treated with the targeted peptide; portion A of FIG. 12, the targeted peptide is L-P-Fe$_3$O$_4$; portion B of FIG. 12, the targeted peptide is SP-94-P-Fe$_3$O$_4$; portion C of FIG. 12, the targeted peptide is a combination of L-P-Fe$_3$O$_4$ and SP-94-P-Fe$_3$O$_4$ with 1:1 ratio.

If HepG2 cells were fixed by formalin, treated with Triton X-100 and stained with L-P-Fe$_3$O$_4$, many tumor cells were stained by a blue reaction product (portion A of FIG. 11); but if the culture cells were stained by SP-94-P-Fe$_3$O$_4$, the stained cell number was lower than that of the L-P-Fe$_3$O$_4$ treated case (portion B of FIG. 11). However, when the HepG2 were stained by a combination of L-P-Fe$_3$O$_4$ and SP-94-P-Fe$_3$O$_4$ with 1:1 ratio, more tumor cells were stained (portion C of FIG. 11). Similarly, if Huh-7 cells after fixation and treated by the same condition, L-P-Fe$_3$O$_4$ (portion A of FIG. 12) stained cell number is somewhat a little more than that of SP-94-P-Fe$_3$O$_4$ stained case (portion B of FIG. 12); while the combination of both peptide linked Fe$_3$O$_4$ showed slightly higher stained cell number than the individual peptide (portion C of FIG. 12). These results show that L-P-Fe$_3$O$_4$ can clearly bind to its targeted protein on the hepatoma cell membrane.

These findings suggest that the L-peptide and SP-94-peptide can specifically bind to their binding protein expressed on the tumor cell membrane and cytoplasm but not on the normal mononuclear cell and hepatocytic plasma membranes (live cell membranes). It also suggests that those peptides are the excellent peptides which could be used for peptide targeted chemotherapy. Since the expression of the peptide targeted binding protein in each tumor cell is different, therefore, the staining pattern on each tumor cell surface is also different.

Example 13: Localization of the Peptide-Targeted Protein in Hepatocellular Carcinoma (HCC) Surgical Specimens For hepatocellular carcinoma surgical specimens, after the deparaffinization of the paraffin-embedded sections and retrieval of targeted protein molecule, as part of the routine immunohistochemistry described as above-mentioned, the sections were incubated overnight with (a) The L-P-Fe$_3$O$_4$ (40 µg per mL); (b) SP-94-P-Fe$_3$O$_4$ (40 µg/mL); (c) one to one ratio of (a) and (b), then with routine Prussian blue reagents, followed by a counter staining for 2 min with nuclear fast red solution. The present invention has used this method to examine 30 hepatocellular carcinoma surgical specimens without difficulty. To count the positive stained cell number of the Prussian blue stained cells in each paraffin section, which are counted 10 high power fields (×400).

Figure 13:
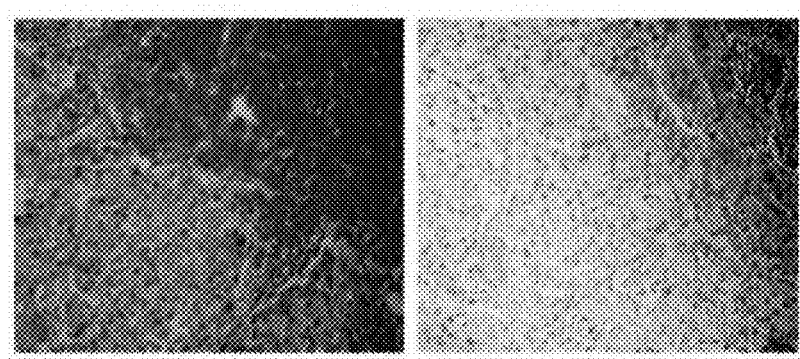
FIG. 13 is the image of Prussian blue staining for hepatocellular carcinoma (HCC) surgical specimens treated with SP-94-P-Fe$_3$O$_4$. Portion A of FIG. 13 is a normal liver section with focal hemorrhage. Portions B, C, D of FIG. 13 are taken from different areas of hepatoma sections.
Figure 13:
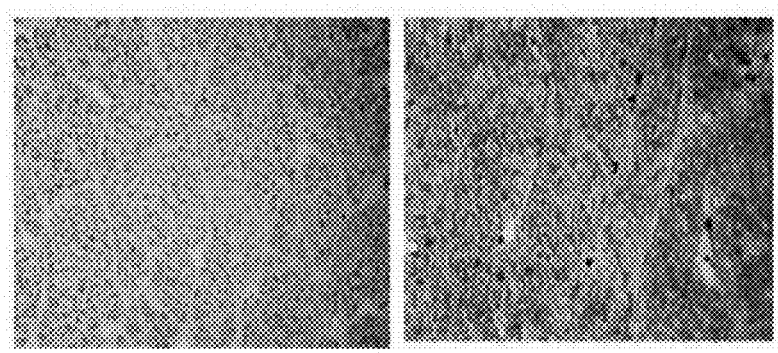
Figure 14:
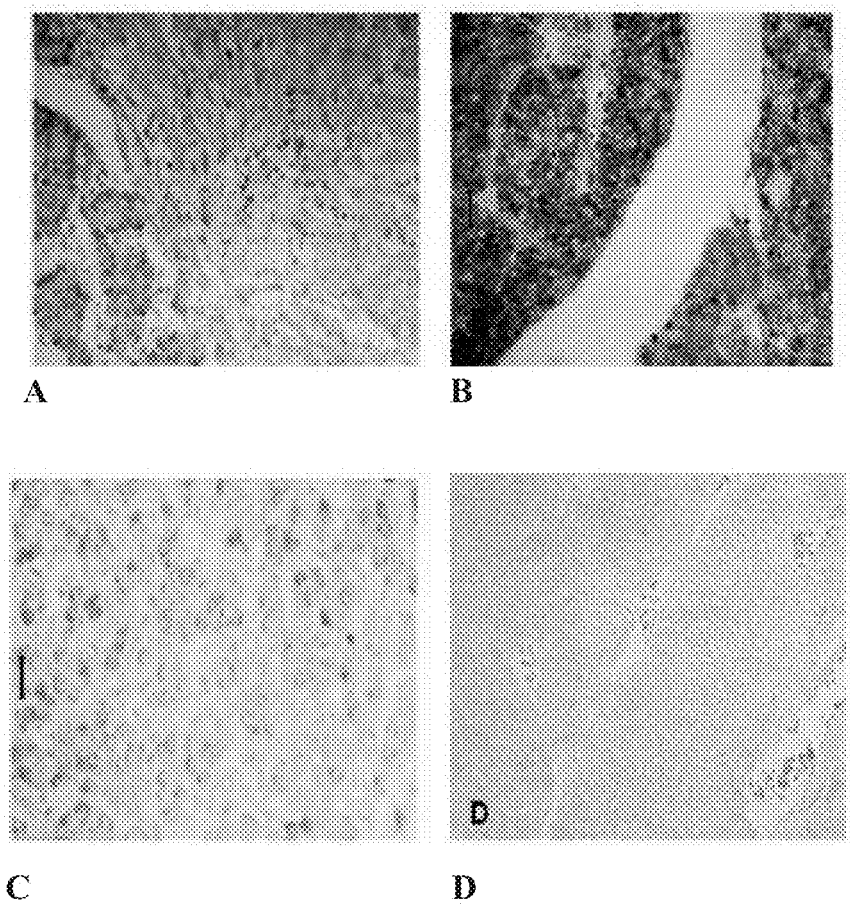
FIG. 14 is the image of Prussian blue staining for HCC surgical specimens treated with L-P-Fe$_3$O$_4$. Portions A to D of FIG. 14 are taken from different areas of hepatoma section.

The results showed that the Prussian blue reaction product was easily identified in the tumor cells in stained sections (portions A and B of FIG. 13); while some tumor cells that had infiltrated the surrounding liver tissue also revealed reaction product (portions A-D of FIG. 13); however, some other tumor cells in the tumor nests and the stromal cells showed no staining (portions A-C of FIG. 13); when SP-94-P-Fe$_3$O$_4$ was used to stain the surgical specimens, the staining pattern was the same as L-P-Fe$_3$O$_4$ staining (portions A-D of FIG. 14). There were approximately 70% to 90% of the tumor cells in each of 30 cases of hepatoma surgical sections revealed reaction products (Table 1). When two kinds of peptide-Fe$_3$O$_4$ were combined to stain the sections, the results showed slightly higher stained cell members in the sections (data not shown). However, some unstained tumor cells were still presented. These results show that L-peptide can also bind to many hepatoma tumor cell cytoplasm in the tumor mass section, the infiltrating tumor cells surrounding normal hepatocytes, and the cytoplasm of infiltrating mononuclear cells.

TABLE 1

Comparison of the staining results from peptide histochemisty by different peptide linked liposomal iron oxide

| | Average percentage of stained tumor cell number | | |
|---|---|---|---|
| Peptide | <25% | 25-50% | >75% |
| L-P-$Fe_3O_4$ | 6 | 7 | 17 |
| SP-94-P-$Fe_3O_4$ | 5 | 9 | 16 |

N = 30
Ten HPV (x 400)

In Table 1, when the stained cell number in each of 30 hepatoma cases was counted, the L-peptide-L-$Fe_3O_4$ stained cell number showed more than 75% stained tumor cells in 17 cases of biopsy specimens, and less than 25% stained cells in 6 cases; while in SP-94-p-L-$Fe_3O_4$ staining, 16 cases have more than 75% stained cells, 9 cases containing 25-50% stained cells, and 5 cases containing less than 25% stained cells. This analysis of stained tumor cell numbers in the surgical specimens of hepatoma showed no significant difference between the binding of each peptide, Therefore, we used L-peptide to perform MRI analysis of hepatoma xenografts and peptide targeted chemotherapy.

Example 14: MR Imaging Analysis of Hepatocellular Carcinoma Xenografts in SCID Mice Four- to six-week-old male SCID mice were obtained from the Animal Center of NTUH. Each mice was inoculated subcutaneously with $1\times10^7$ cells per 0.2 ml of HepG2 cells on the left flank or right thigh. At day 14 after the injection, a xenograft about 0.8 to 1 diameter in each mouse was observed. For MRI animal examination, a Bruker 7T BioSpec 70/30 USR Preclinical system was also applied in vivo. Under gas anesthesia with 2% Isoflurane, each mouse was placed in a homemade resonance coil with an inner diameter of 3.7 cm. Gradient echo pulse sequences provided by the vendor were used (TR/TE 5000/56 ms, Matrix size 256×256). The slice thickness was 1 mm with a 1 mm gap, and the FOV was 9×3.5 cm. The total scan time was 10 min and 40 s at the NEX of 4. Then 2 mg in 0.2 ml of L-P-$Fe_3O_4$ per kg of mouse body weight was injected into the tail veins of 5 male SCID mice. The mice underwent magnetic resonance imaging examination 24 hours after the injection. Precontrast and postcontrast signal intensities of NPC xenografts were measured and tested using Image J software (NIH, Bethesda. U.S.A).

Figure 15:
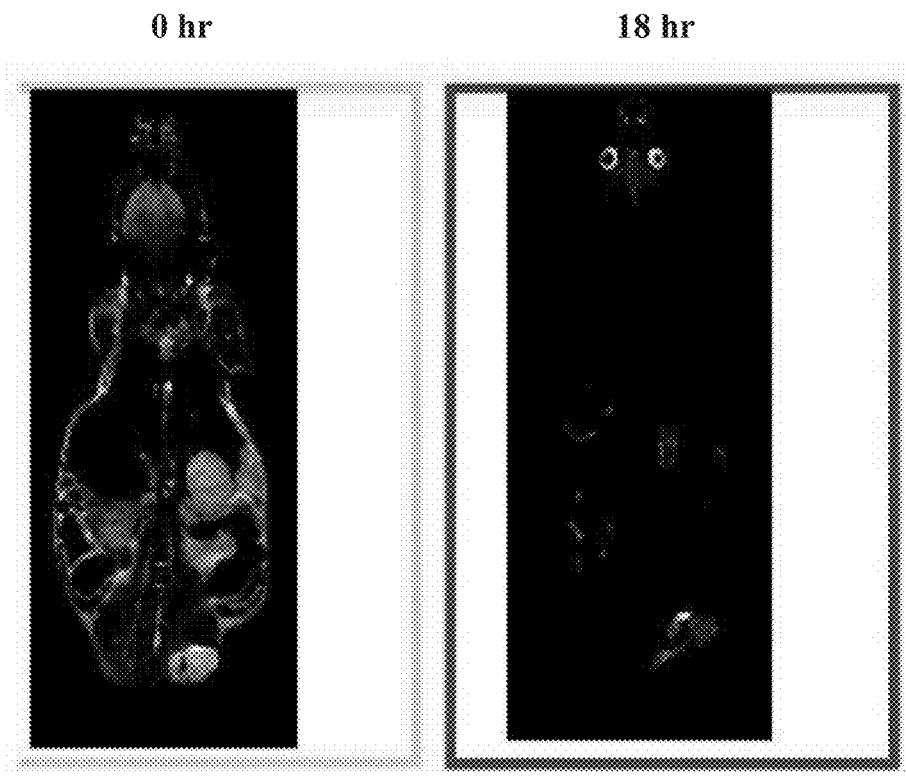
FIG. 15 is the MR imaging analysis of hepatocellular carcinoma xenografts in SCID mice. Right figure is the MR imaging analysis of hepatocellular carcinoma xenografts in SCID mice after 18 hr injection with L-P-Fe$_3$O$_4$. Lift figure is the MR imaging analysis of hepatocellular carcinoma xenografts in SCID mice before injection.

When the HepG2 xenografts were analyzed by a T2-weighted MRI before and after 18 hr injection with L-P-$Fe_3O_4$, the image intensity of the xenografts in the injected animals showed a lower signal intensity of the xenograft masses (FIG. 15, right) compared with the imaging before injection (FIG. 15, left). These results indicate that the usage of L-peptide linked iron oxide for identification of hepatoma nodule in the patient is possible clinically.

Figure 16:
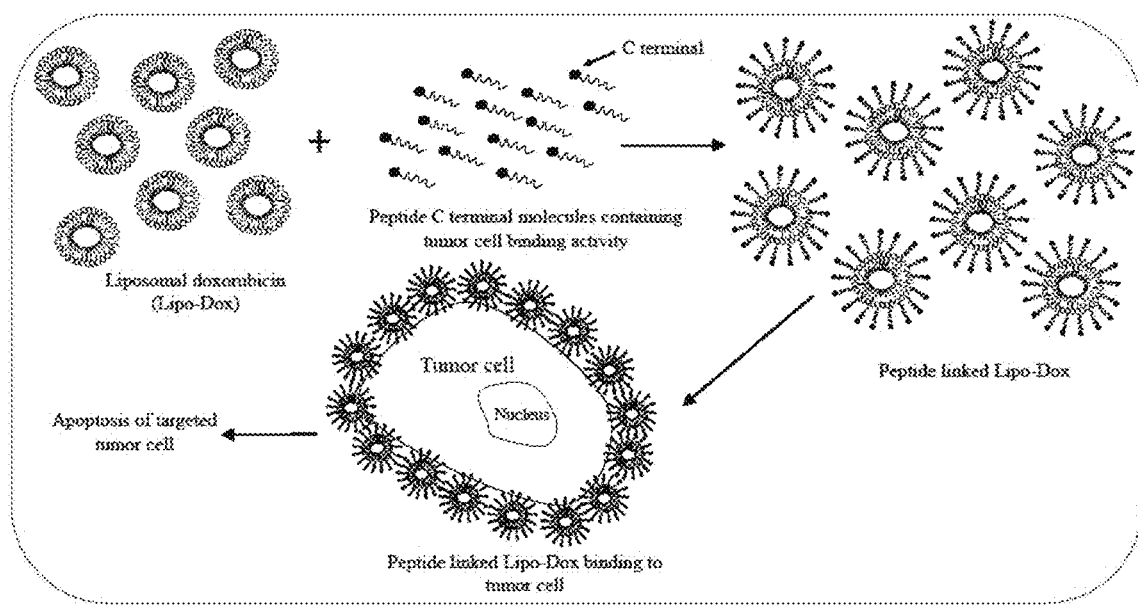
FIG. 16 shows the method for preparation of peptide linked liposomal doxorubicin to bind to cancer cells and to induce apoptosis.

Example 15: Efficacy of L-Peptide-Liposomal-Doxorubicin (L-P-L-D), SP-94-Peptide-Liposomal-Doxorubicin (SP-94-P-L-D) and PC5-52-P-L-D (PC5-52-Peptide-Liposomal-Doxorubicin) Treatments for SCID Mice Bearing HepG2 Xenografts The purpose of this embodiment was to use the peptide targeting chemotherapy to overcome the adverse event in the conventional targeted chemotherapy for human hepatocellular carcinoma. As shown in FIG. 16, those peptides were linked to liposomal iron oxide nanoparticles to localize the targeted tumor cells and endothelia, and linked to dextran coated liposomal doxorubicin to treat SCID mice bearing hepatoma xenografts.

For the peptide targeted chemotherapy, 40 male SCID mice were transplanted with $1\times10^7$ HepG2 cells into their right thigh subcutaneously; after 10 days, solid xenografts measuring approximately 0.8 cm in diameter were found in each mouse, then they were divided into four groups (each group included 10 mice). The first group was injected with PBS; the second and third groups were injected either with L-P-L-D or PC5-52-P-L-D, separately. Each dose contained 2 mg doxorubicin/kg of mouse body weight. The fourth group mice were injected with L-P-L-D (1 mg doxorubicin/kg) mixed with PC5-52-P-L-D (1 mg doxorubicin/kg). All doses were injected through the tail vein, once per week, for a total of 4 injections, and all animals were sacrificed at day 35. The body weight and tumor size were measured weekly. All animals were examined by routine autopsy. The xenograft tumors and all visceral organs were examined by histopathological sections after stained by hematoxylin and eosin. The pegylated peptide was linked to L-D in our laboratory according to our previously published methods (Cancer Res. 64:8002-8008, Nov. 1, 2004). For comparison, another animal experiment was performed. In the later experiment, the present invention used NSG (NOD-SCID immunodeficiency gamma strain animals); the experiments were totally similar to the NOD SCID mice case. In addition, the present invention has also used two combinations of L-P-L-D and SP-94-P-L-D, to treat the xenograft bearing mice using 0.5 mg/kg of L-P-L-D and 0.5 mg/kg of SP-94-P-L-D in one group and 2 mg/kg of L-P-L-D and 2 mg/kg of SP-94-P-L-D in another group, once per week, to treat the NSG mice, 5 weeks in total and then the animals were sacrificed for histopathological examination.

Figure 17:
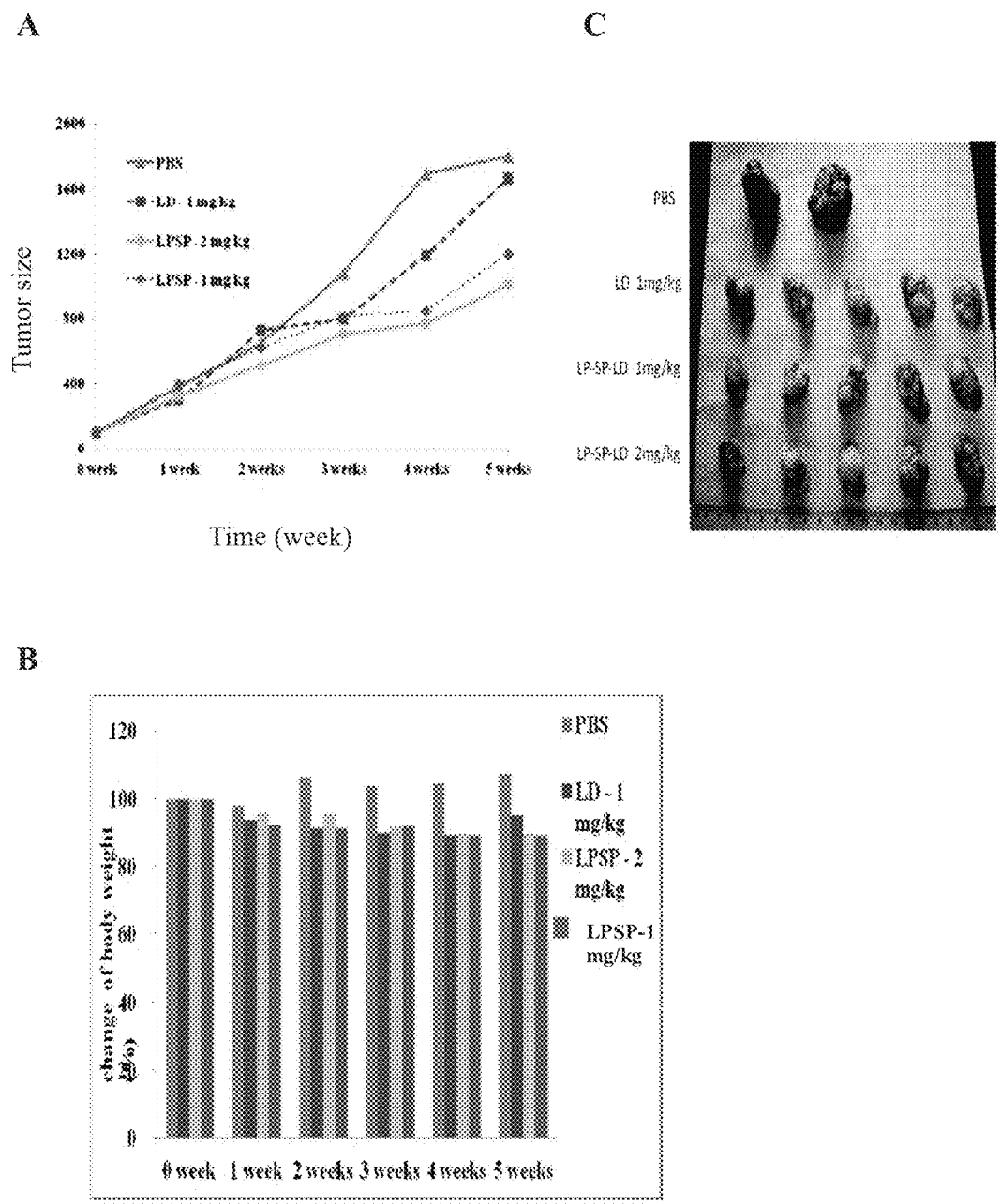
FIG. 17 shows the efficacy of the combination of L-P-L-D and SP-94-P-D at 1 mg or 2 mg of L-D/kg body weight treatments for SCID mice bearing HepG2 xenografts. Portion A of FIG. 17 shows tumor size change; Portion B of FIG. 17 shows body weight change; and Portion C of FIG. 17 shows histopathologocal pictures.

When the SCID mice bearing HepG2 xenografts were treated once a week for a total of 4 weeks with PBS (PBS), 1 mg/kg L-D body weight (LD 1mg/kd) or the combination of L-P-L-D and SP-94-P-D at 2 mg of L-D/kg body weight (LP-SP-LD 2 mg/kg) and the combination of L-P-L-D and SP-94-P-D at 1 mg of L-D/kg body weight (LP-SP-LD 1 mg/kg), the size of the xenografts treated with the combination of L-P-L-D and SP-94-P-D at 1 mg or 2 mg of L-D/kg body weight has reduced 85% in the L-P-L-D group when compared with PBS group (portion A of FIG. 17). No significant different change of body weight was shown in those 4 groups portion B of FIG. 17). The average of xenograft weight showed a ratio of PBS:L-D:L-P-L-D:SP-94-P-L-D=1:03:02:02. However, the histopathologocal pictures of the xenografts in the L-D, L-P-L-D, the combination of L-P-L-D and SP-94-P-L-D groups revealed a markedly different feature (portion C of FIG. 17). In the PBS control group, tumor cells with ischemic necrosis were found in the central part of the tumor. But the peripheral parts are all normal. In the L-D-treated group, tumor necrotic and apoptotic areas were localized in the central part and extended to some peripheral part of the xenograft, whereas the other parts of the xenograft revealed original tumor cells with many mitotic features. In the combination of L-P-L-D and SP-94-P-L-D treated group, it showed marked tumor necrosis and disseminated apoptosis in the whole xenograft. In the visceral organs, which included the cardiac muscle, the liver, the kidney, the spleen and the bone marrow, the L-P-L-D and the combination of L-P-L-D and SP-94-P-L-D treated groups all showed no clear abnormalities, while in the L-D-treated group, although the bone marrow and cardiac muscle showed no specific change, but the liver revealed sporadic vesicular degeneration in most of hepatocytes with some apoptotic change in some hepatocytes; the kidney also showed focal necrosis and apoptosis of some proximal tubular epithelia. Additionally, the spleen also revealed apoptotic changes in certain megakaryocytes (data not shown). It is apparent that a combination of two different peptides linked L-D is better than a single peptide-L-D to kill hepatoma cells. On the other hand, the present invention has also use the combination of 0.5 mg/kg of L-P-L-D and 0.5 mg/kg of PC5-52-P-L-D, and the combination of 1 mg/kg of L-P-L-D and 1 mg/kg of PC5-52-peptide to treat the hepatoma xenograft bearing NSG mice. The result was even better than that of the combination of L-P-L-D and SP-94-P-L-D in NON-SCID mice. In addition, the present invention has also injected L-P-L-D 0.5 mg/kg per day for 4 days, followed by 0.5 mg/kg of PC5-52-P-L-D per day for another 3 days, and 1 mg/kg of L-P-L-D per day for 4 days plus PC5-52-P-L-D 1 mg/kg per day for 3 days. The results were also better than the combination of L-P-L-D and SP-94-P-L-D treatment.

To evaluate the optimal dose of drugs for a high efficacy with minimal adverse event with L-P-L-D treatment in SCID mice bearing HepG2 xenografts, the present invention found that 1 mg of L-D (liposomal-doxorubicin)/kg body weight could partially inhibit tumor growth; however, if 2 mg of L-D was used, the tumor size was markedly reduced. The present invention also found that if a combination of L-P-L-D and SP-94-P-L-D was used, the efficacy was even better than the above mentioned treatment (portion A of FIG. 15). In addition, if the SP-94-P-L-D was combined with PC5-52-P-L-D, the result also revealed a pretty high efficacy of chemotherapy for hepatoma.

On the other hand, if the experiment using the combination of SP-94-P-L-D and PC5-52-P-L-D to treat the xenograft bearing mice once per week for 6 weeks, the efficacy was no better than that of one week was injected with SP-94-P-L-D and the $2^{nd}$ week injected with PC5-52-P-L-D, and then alternatively injected with the first preparation and then with $2^{nd}$ preparation, the efficacy of xenograft treatment was even better than that of the combination of two peptide linked L-D injection per week.

The peptides L-P-L-D or SP-94-P-L-D in combination with PC5-52-P-L-D could inhibit tumor growth with no specific adverse event, wherein L-peptide and SP-94-peptide target anti-hepatoma cell membrane, PC5-52-peptide target anti-tumor endothelia. However, when the control peptide was used, the xenograft size was also decreased, but the visceral organs revealed marked apoptotic change. Accordingly, the specific L-P-L-D or SP-94-P-L-D in combination with PC5-52-P-L-D can be used for treatment of SCID mice bearing hepatoma xenograft with minimal adverse event.

What is claimed is:

1. A method of reducing the side effects of cancer chemotherapy by using peptides, comprising:
   administering to a subject suffering from a cancer and effective amount of a chemotherapeutic drug and peptides;
   wherein the peptides are at least two selected from the group consisting of amino acids of SEQ ID NO: 1, SEQ ID NO: 2, and SEQ ID NO: 6; and
   wherein the administering step is consecutive administration.

2. The method according to claim 1, wherein the cancer is liver cancer, pancreatic cancer or lung cancer.

3. The method according to claim 1, wherein the peptides are amino acid sequences of SEQ ID NO:2 and SEQ ID NO:6.

4. The method according to claim 1, wherein the peptides are amino acid sequences of SEQ ID NO:1 and SEQ ID NO:6.

5. The method according to claim 1, wherein the peptides are amino acid sequences of SEQ ID NO:1 and SEQ ID NO:2.

6. The method according to claim 1, wherein the chemotherapy drug is selected from the group consisting of carboplatin, cisplatin, oxaliplatin, cyclophosphamide, dacarbazine, temozolomide, gemcitabine, capecitabine, cladribine, clofarabine, cytarabine, floxuridine, fludarabine, hydroxyurea, methotrexate, pemetrexed, pentostatin, thioguanadine, daunorubicin, doxurubicin, epirubicin, idarubicin, topotecan, irinotecan, etoposide, eniposide, colchicine, vincristine, vinblastine, vinorelbine, paclitaxel, docetaxel, and a combination thereof.

* * * * *

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Arg Leu Leu Asp Thr Asn Arg Pro Leu Leu Pro Tyr
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide

<400> SEQUENCE: 2

Ser Phe Ser Ile Ile His Thr Pro Ile Leu Pro Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide

<400> SEQUENCE: 3

Arg Leu Leu Asp Thr Asn Arg Pro Leu Gly Gly Gly
1               5                   10
```

```
<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Thr Lys Ser Gly Gly
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide

<400> SEQUENCE: 5

Arg Leu Leu Asp Thr Asn Arg Gly Gly Gly Gly Gly
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide

<400> SEQUENCE: 6

Ser Val Ser Val Gly Met Lys Pro Ser Pro Arg Pro
1               5                   10
```